Figure 1:
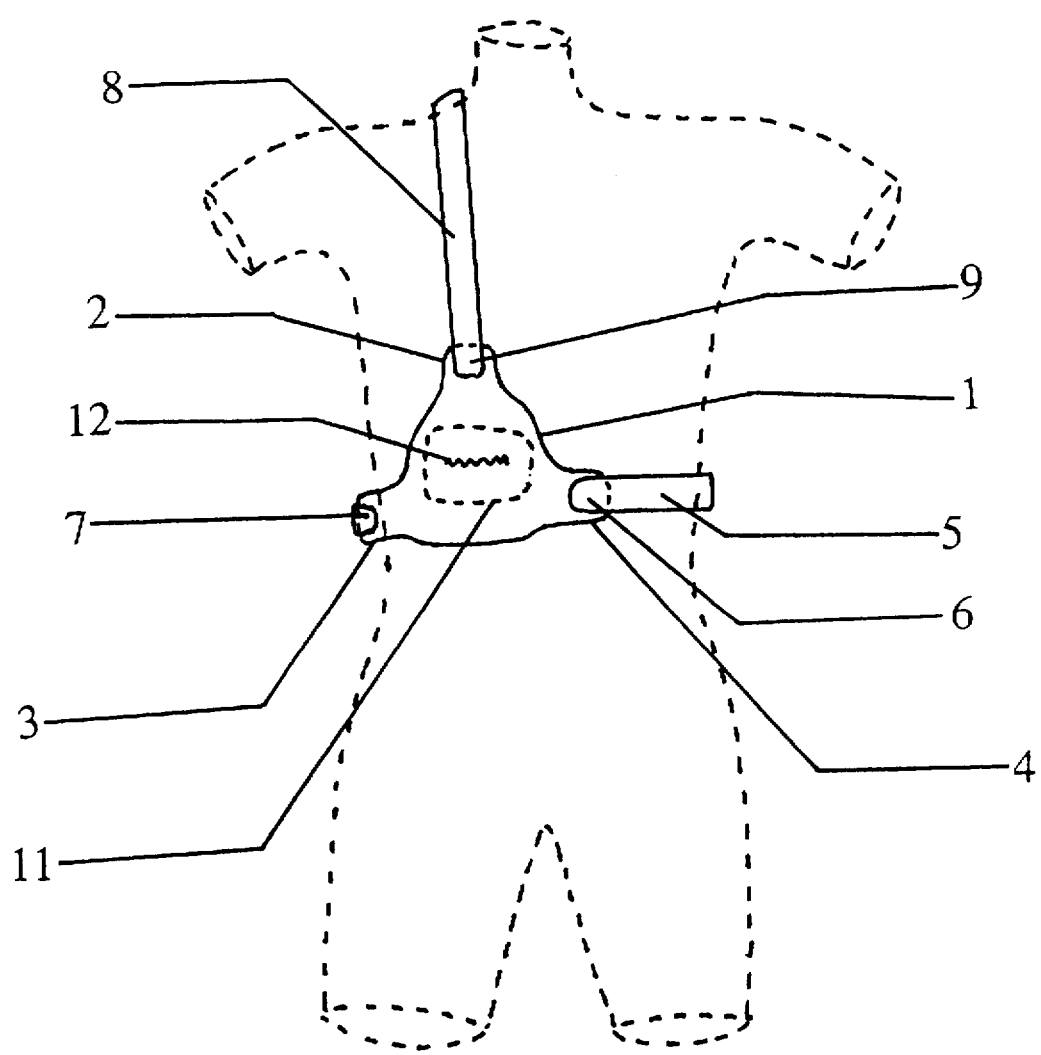

United States Patent [19]

Daneshvar

[11] Patent Number: 5,779,657
[45] Date of Patent: Jul. 14, 1998

[54] NONSTRETCHABLE WOUND COVER AND PROTECTOR

[76] Inventor: Yousef Daneshvar, 21459 Woodfarm, Northville, Mich. 48167

[21] Appl. No.: 505,538
[22] Filed: Jul. 21, 1995
[51] Int. Cl.⁶ .................................................. A61F 5/00
[52] U.S. Cl. ................................................ 602/60; 602/79
[58] Field of Search .................................... 606/201, 202, 606/203; 602/42, 43, 53, 75, 79, 60–63, 19

[56] References Cited

U.S. PATENT DOCUMENTS

| | | | |
|---|---|---|---|
| 2,814,295 | 11/1957 | Hasse | 602/79 X |
| 3,270,742 | 9/1966 | Costa | 602/79 |
| 4,917,112 | 4/1990 | Kalt | 602/42 |
| 5,086,763 | 2/1992 | Hathman | 602/79 X |
| 5,372,589 | 12/1994 | Davis | 604/180 |
| 5,456,660 | 10/1995 | Reich et al. | 602/79 |
| 5,464,420 | 11/1995 | Hori et al. | 606/202 |
| 5,470,000 | 11/1995 | Muñoz | 602/19 X |
| 5,538,502 | 7/1996 | Johnstone | 602/79 |

Primary Examiner—Richard J. Apley
Assistant Examiner—Kim M. Lee

[57] ABSTRACT

This application considers the problem of the wound care and it introduces a series of support units that will allow for easy, transparent, controlable wound care to be done. The unit also indicates how a pressure applying means can be used to compress the wound site for prevention of bleeding and a better wound care. Importantly, in some models these units will have properties that are designed to detect bleeding if it occurs.

23 Claims, 16 Drawing Sheets

NONSTRETCHABLE WOUND COVER AND PROTECTOR

Please notice that this application is related to the applicant's previously approved or pending applications, and the content of the following application is incorporated by reference as if it were fully disclosed herein. The applicants previous inventions are as follows: D. Device, Pressure bandages and dressings, Latex Support, D. Device 2, D. Device 3, D. Device 4, D. Device 5, and D. Device 6, Daneshvar's Device 7, Daneshvar's Device 8 and Daneshvar's Device 9.

The application for D. Device was applied on Nov. 29, 1991. A patent is issued with U.S. Pat. No. 5,263,966.

The application for Pressure Bandages and dressings was applied on Oct. 28, 1992 with The application for D. Device 2 was applied on Dec. 14, 1992, and it was renamed as "Device for preventing post-catheterization wound bleeding." A patent is issued with U.S. Pat. No. 5,423,966.

The application for D. Device 3 was applied on Apr. 5, 1993, and it was renamed as "Device for preventing post-catheterization wound bleeding." A patent is issued with U.S. Pat. No. 5,383,893.

The application for D. Device 4 was applied on Aug. 21, 1993, with Ser. No. 08/113,652.

The application for D. Device 5 was applied on Dec. 14, 1993 with Ser. No. 08/165,835.

The application for D. Device 6 was applied on May 5, 1994 with Ser. No. 08/238,629

The application for Daneshvar, Device 7 was applied on 8/8/1994 with Ser. No. 08/287,307.

The application for Daneshvar, Device 8 was applied on Sep. 22, 1994 with Ser. No. 08/310,349.

The application for the Latex Supports was initially applied on Jan 13, 1993, with Ser. No. 08/004,069 and was continued on Sept 19, 1994, with Ser. No. 08/308,824. It is still pending.

The application for Daneshvar's, Device 9 was applied on Jun. 5, 1995, with Ser. No. 08/461,263.

The background of this invention

This invention is related to wound care and prevention of bleeding in the body of humans or animals after cuts, wounds, surgeries, other procedural and therapeutic interventions in which wound care and prevention of bleeding is of prime interest. Commonly, these wounds are covered with gauze pads which are held in place and sometimes compressed by the use of adhesive tapes. However, this method has many problems: the adhesive tapes and materials cause skin reactions, cause pain while being removed, and they simply do not stick well when the area is covered by hair. Furthermore, when there is need for compression of the wound this method simply can not apply enough pressure to the area to control bleeding; such pressure can not be measured, increased or adjusted. This method does not allow the wound site to be seen, and repeating the dressing doubles or triples the problems related to the adhesive tapes. On the other hand, wrapping the gauze around the wound is not easy either; the process is difficult: the patient has to sit up or move up and this takes significant time and energy which should not be spent. For these reasons this applicant has previously made units to solve similar problems and contribute to humanity for a better human life. His previous applications such as D. Device, Pressure Bandages and Dressings, the Latex Support , D. Device 2, D. Device 3, D. Device 4, D. Device 5, D. Device 6, D. Device 7, Daneshvar's Device 8 and 9 are all related to these or similar problems. However, due to the unfamiliarity of the applicant with the procedure of patent applications and the election requirements many important aspects of these units could not claimed in one application. Thus, he would like to introduce this unit which has its own new matters and important elements, and stresses some important points of the previous embodiments as well.

THE BRIEF EXPLANATION OF THE INVENTION

This invention introduces a support unit that is primarily made from a flexible, stretchable or non-stretchable, transparent material which is shaped to match the shape of the anatomy of the area and to stand on the wound site properly. This support unit will then allow the gauze pads, or other therapeutic or compression units to be held in place securely. This unit has end pieces which are designed to allow the unit to be adjustably and removably connected to a series of straps by different means. These straps are designed to go around the limb, part of the body or the trunk in order to hold the support piece in place securely. Alternatively, the support unit may have a band of connection mean such as Velcro (™) patch around it in order to allow the straps to be attached to it in any suitable spot conveniently. This support system will be a stable, secure unit to hold the gauze pads, pressure units or similar diagnostic or therapeutic units in the area securely. The pressure units such as inflatable balloons are of special importance since they will allow the wound site to be compressed in order to prevent bleeding, wound swelling, etc. Some models of these support units will have a door to allow them to be opened for convenient wound care. Importantly, this unit may also use gauze pads with sensors designed to detect bleeding.

The figures. Please notice that in order to prevent a cluttered picture, the applicant did not show all the important options in one picture. However, he would like to indicate that all important aspects of these models are to be utilized by all models, if it applies.

BRIEF MENTIONING OF THE FIGURES

FIG. 1. Shows a patient with a unit on the right upper quadrant over an incision of a gallbladder surgery.

Figure 2:
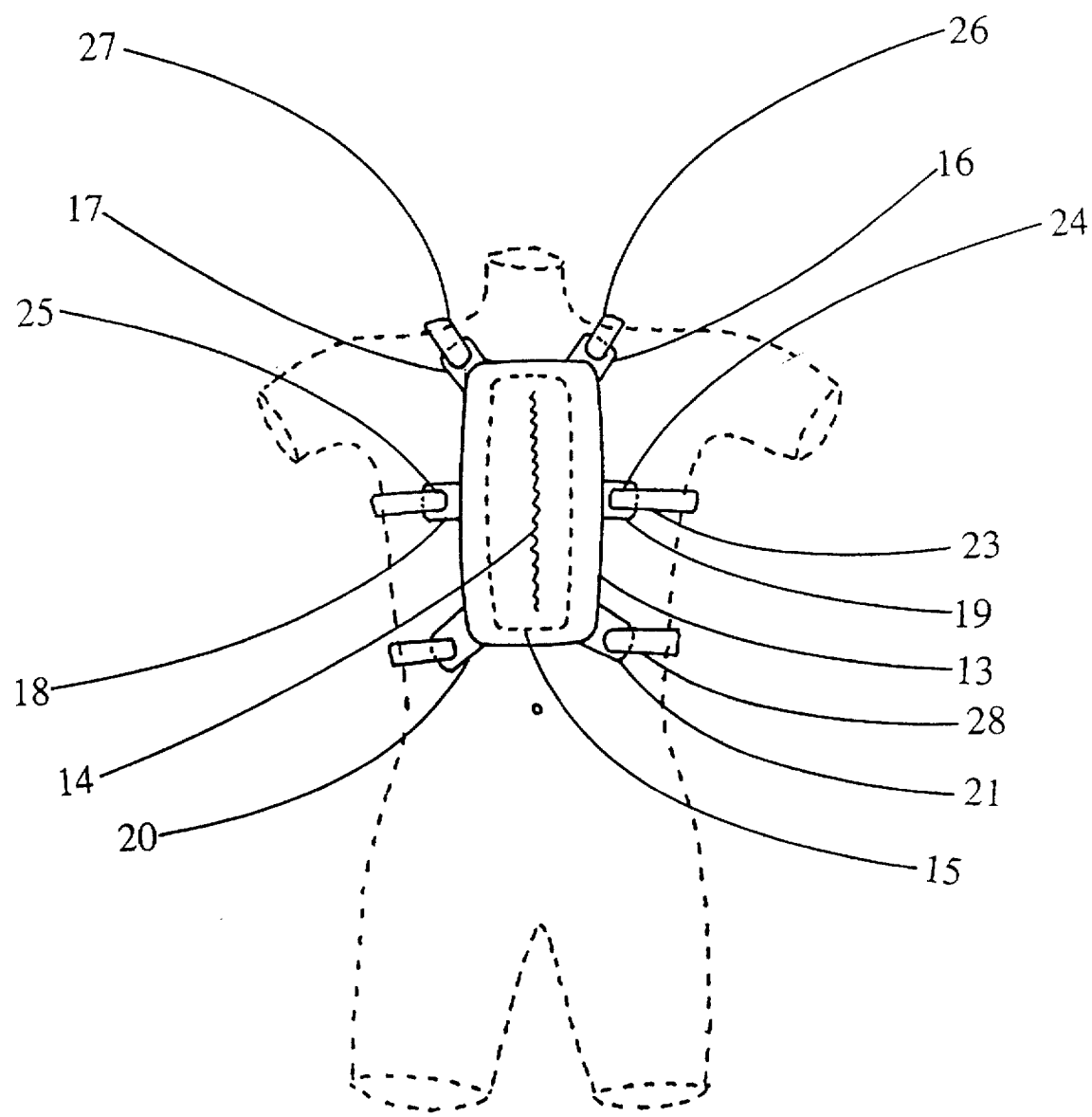

FIG. 2. Shows a unit designed to be used after surgeries in the center of the body.

Figure 3:
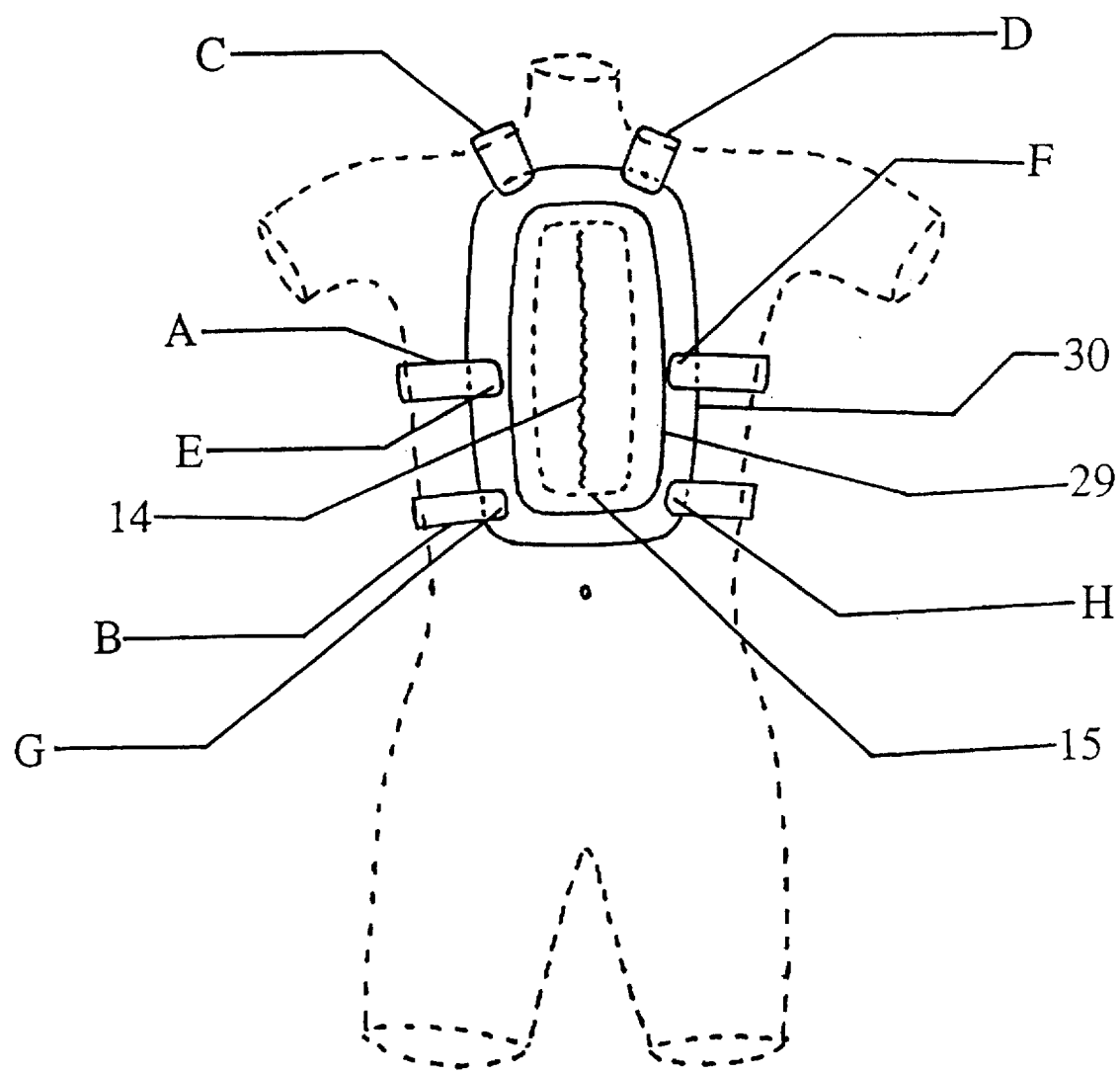

FIG. 3. Shows a unit which has a band of connection mean on its border.

Figure 4:
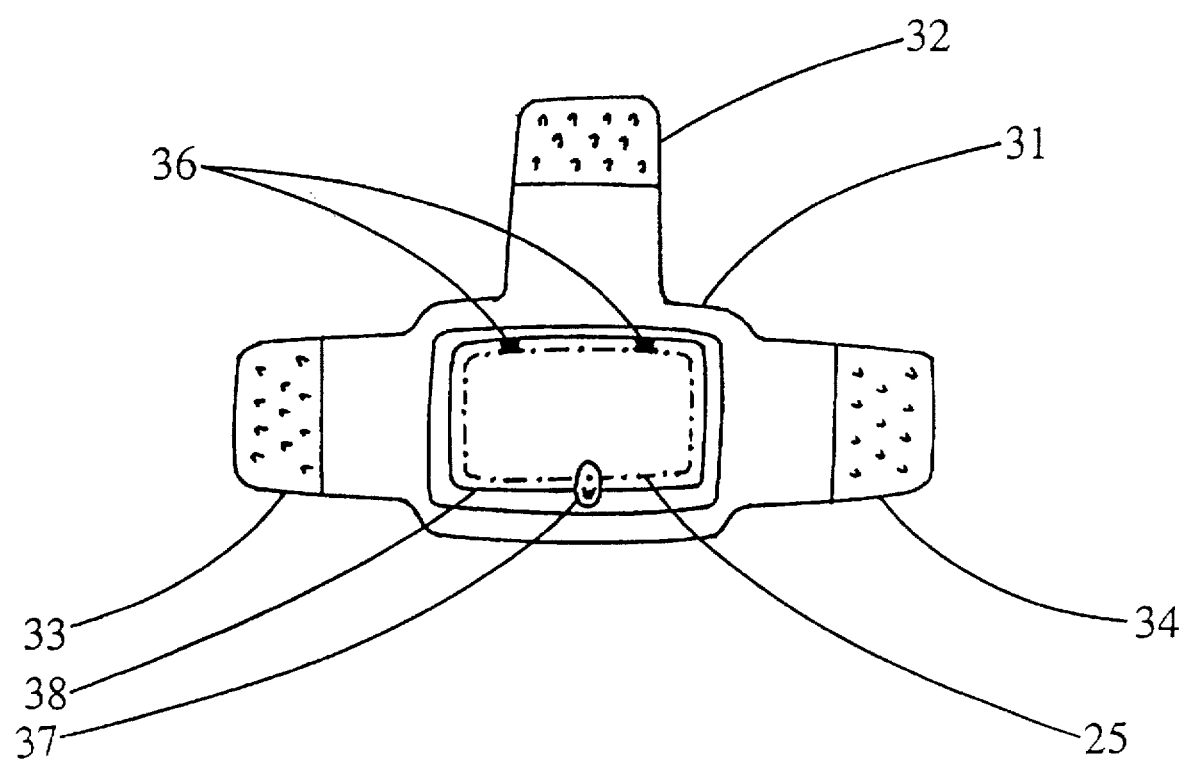

FIG. 4. Shows a unit which has a door mean that holds the gauze pad on the wound site.

Figure 4A:
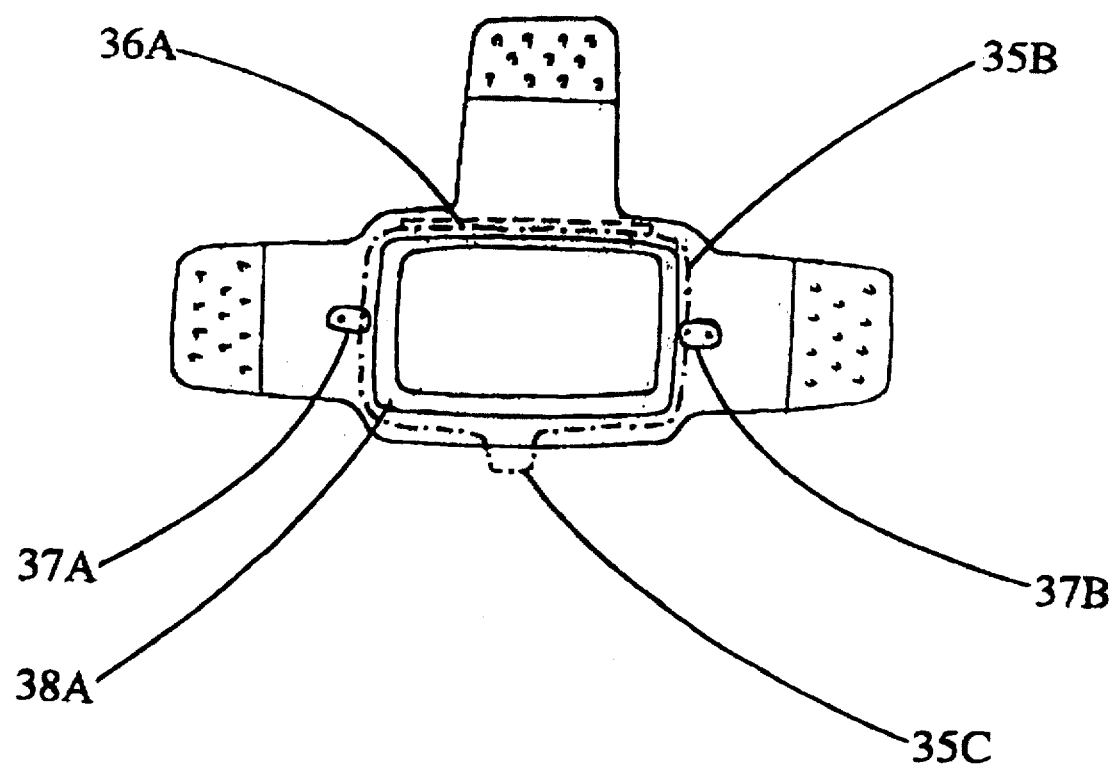

FIG. 4A. Shows a unit which the door is much larger piece and acts as a large cover.

Figure 5:
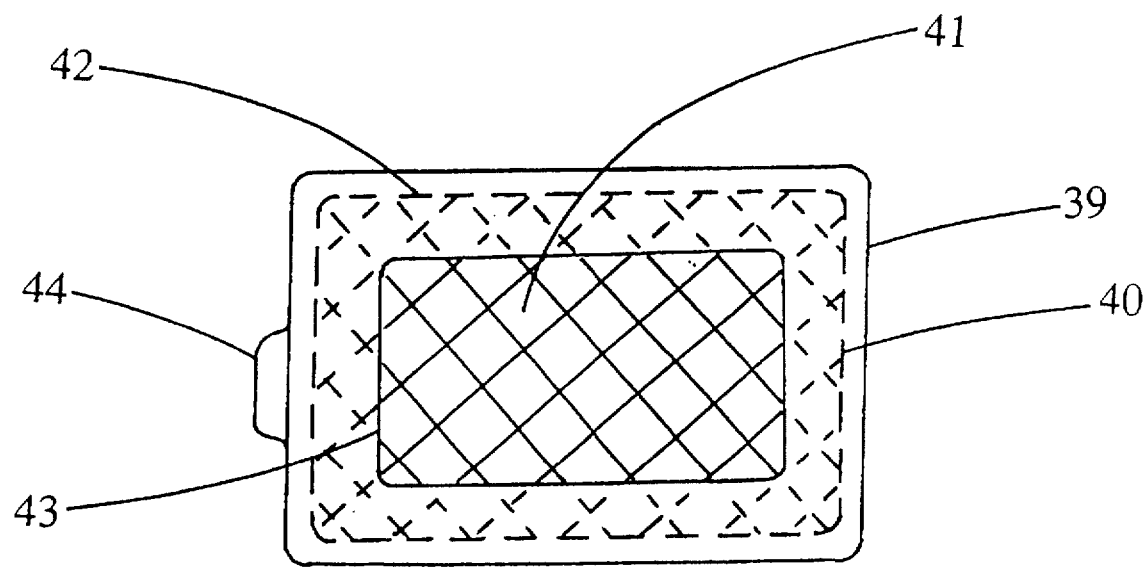

FIG. 5. Shows a gauze pad that has a cover to hold the secretions inside and prevent dripping of the secretions.

Figure 6:
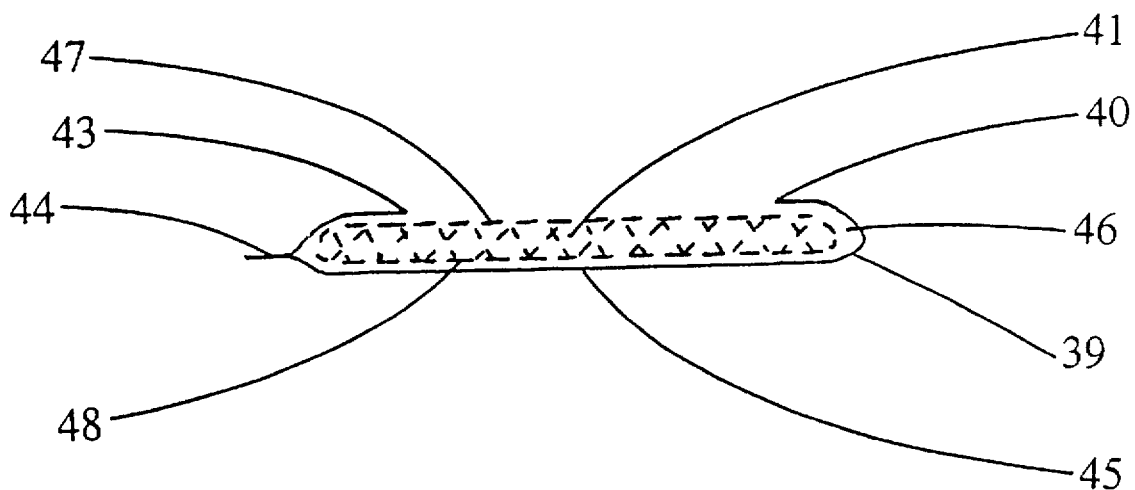

FIG. 6. Shows the cross-cut view of the gauze pad shown in the previous FIG. 5.

Figure 7:
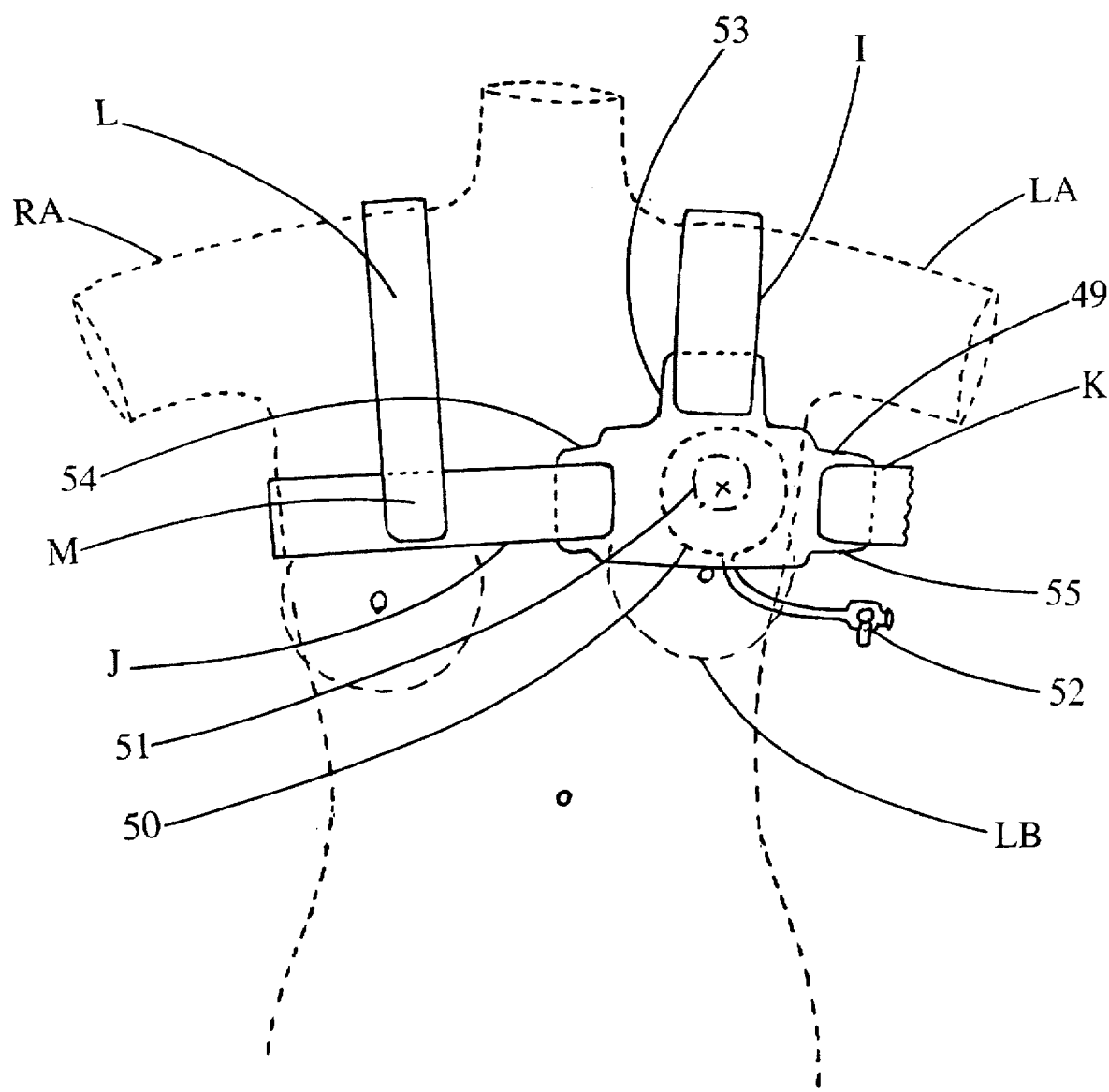

FIG. 7. Shows a unit which holds an inflatable balloon on the wound site.

Figure 8:
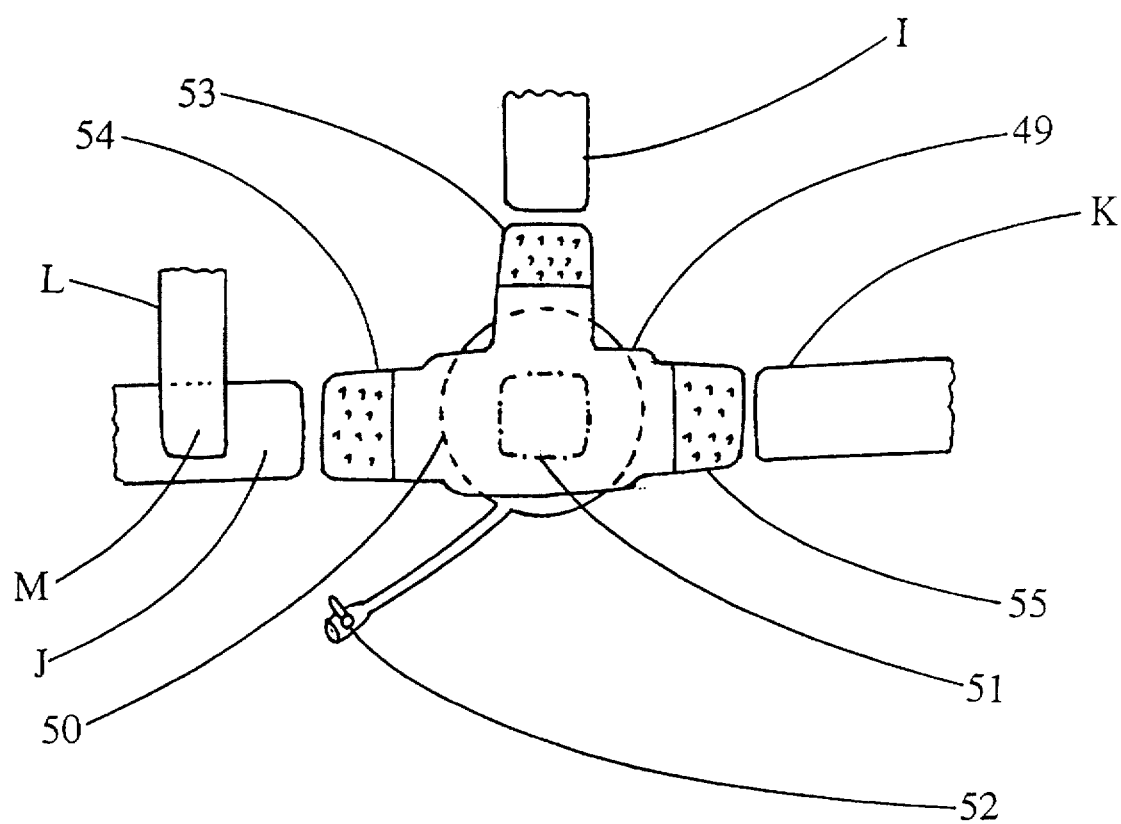

FIG. 8. Shows a unit for procedures in the upper body such as breast procedures.

Figure 9:
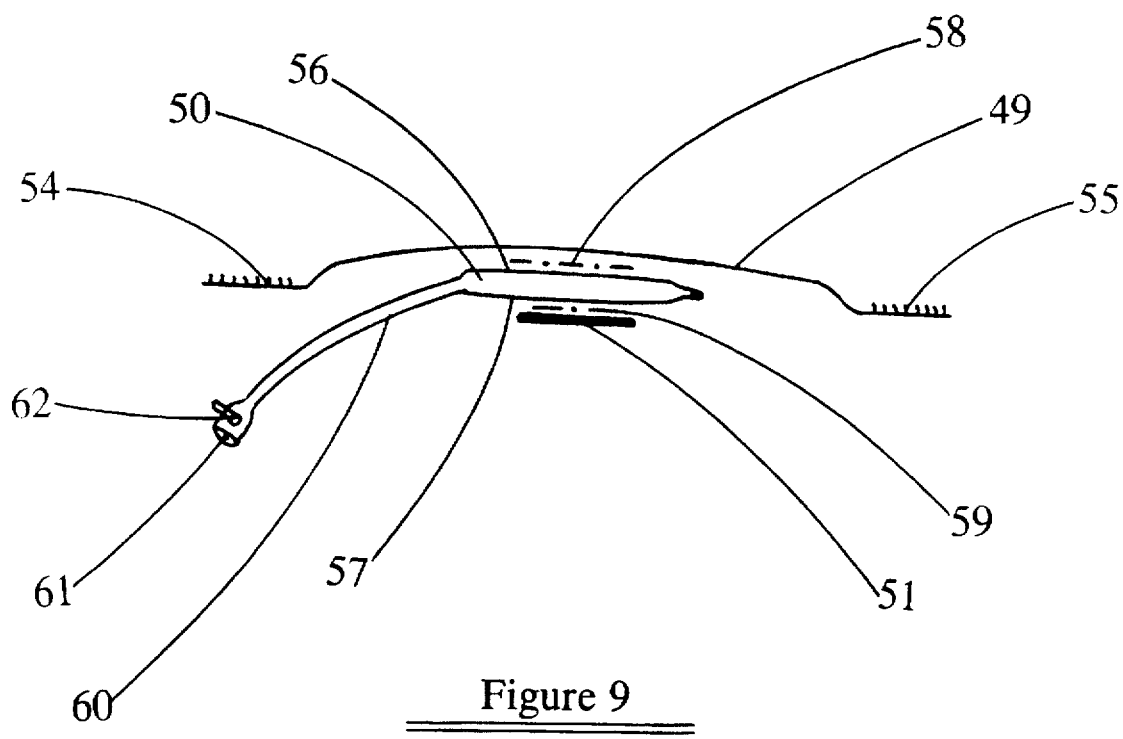

FIG. 9. This FIG. schematically shows a cross-cut view of the unit shown in the previous FIG. 8.

Figure 10:
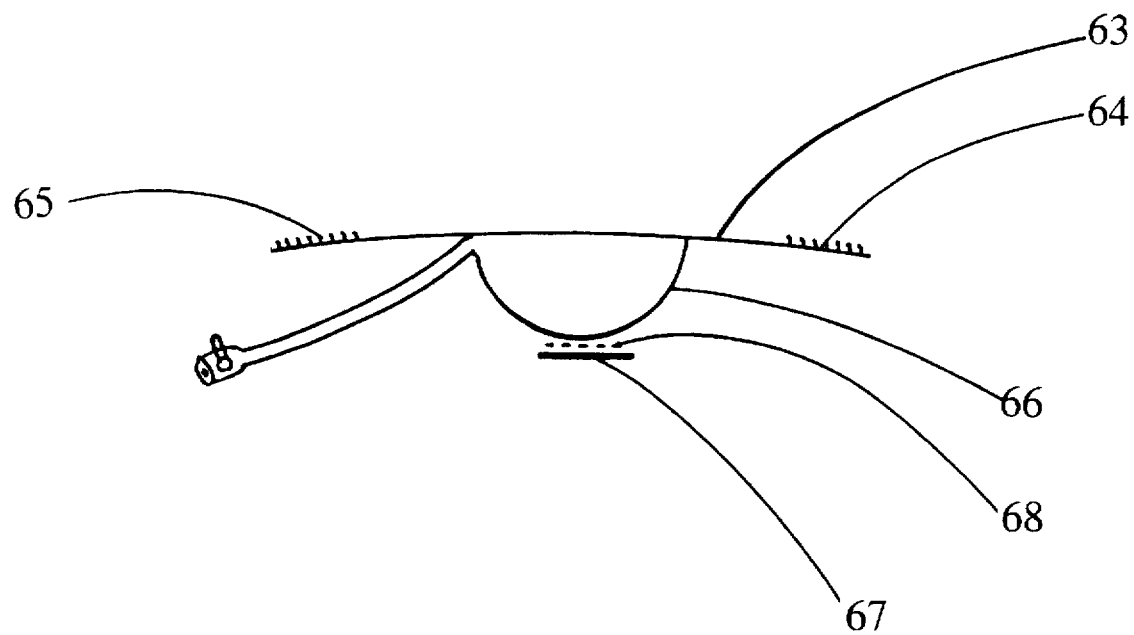

FIG. 10. Shows a unit which has a dome-shaped balloon connected to its body.

Figure 11:
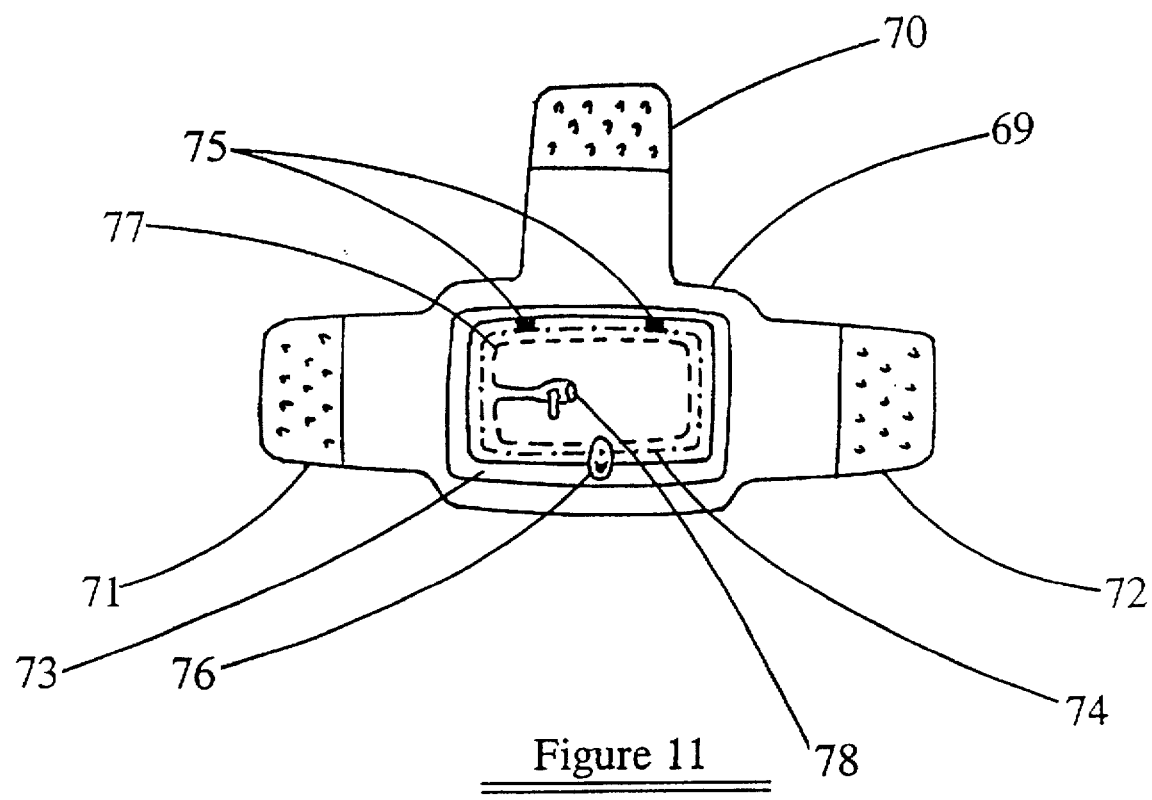

FIG. 11. Shows a unit which has a door and a balloon inside it.

Figure 12:
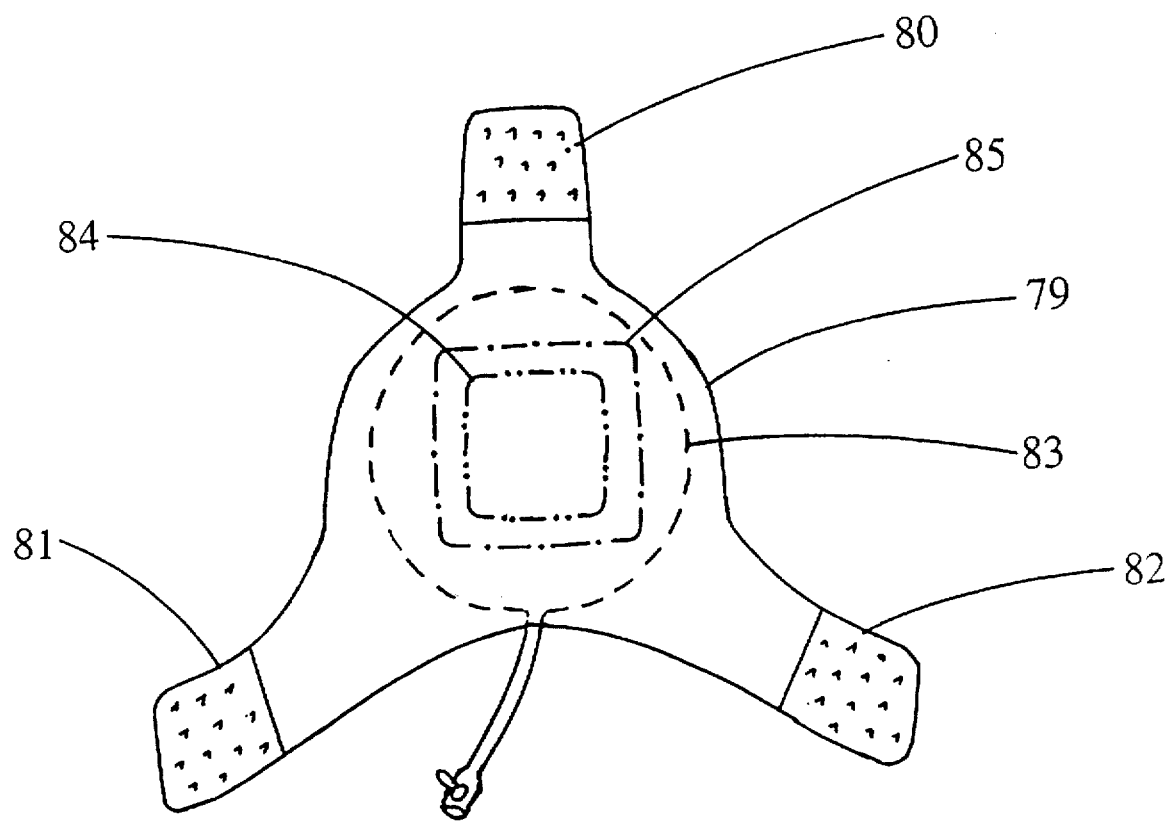

FIG. 12. Shows a unit which has a balloon, a front piece and a wound piece.

Figure 13:
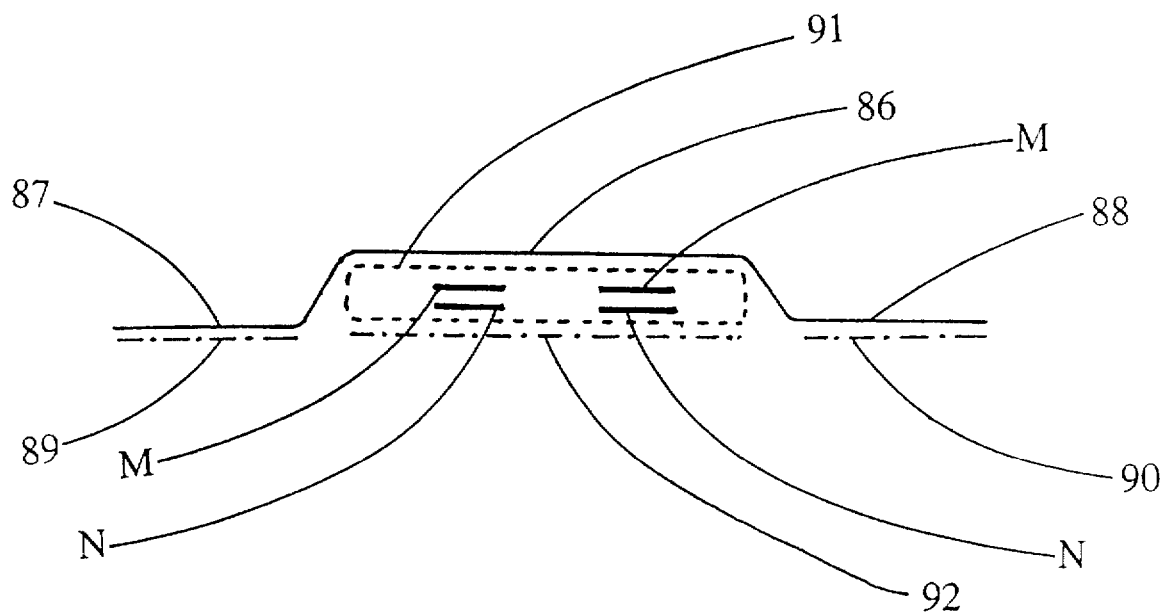

FIG. 13. Shows a unit designed to give a signal if bleeding occurs in the wound site.

Figure 14:
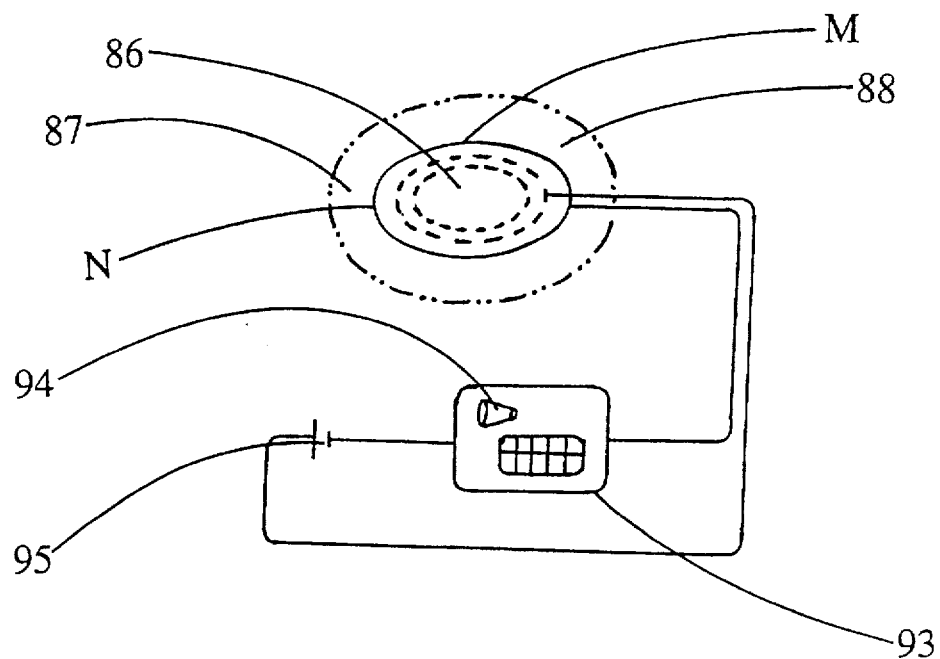

FIG. 14. Shows how the bleeding detection system functions.

Figure 15:
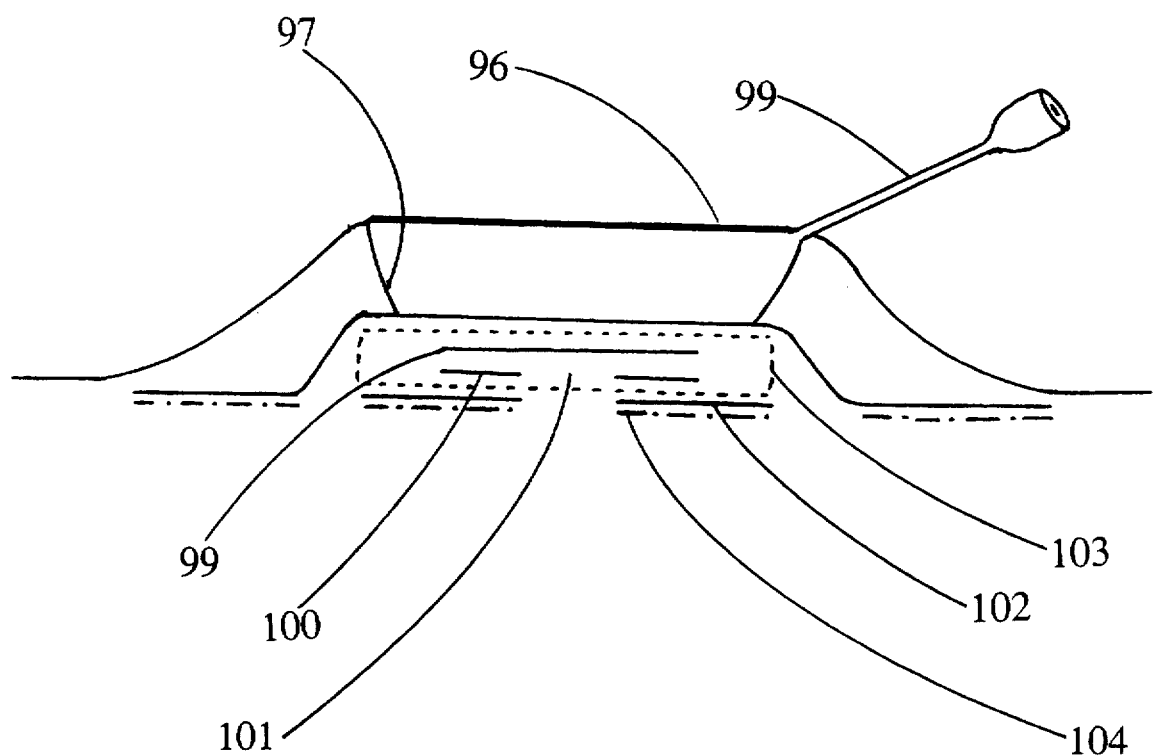

FIG. 15. Shows a wound detection unit and a compression unit.

Figure 16:
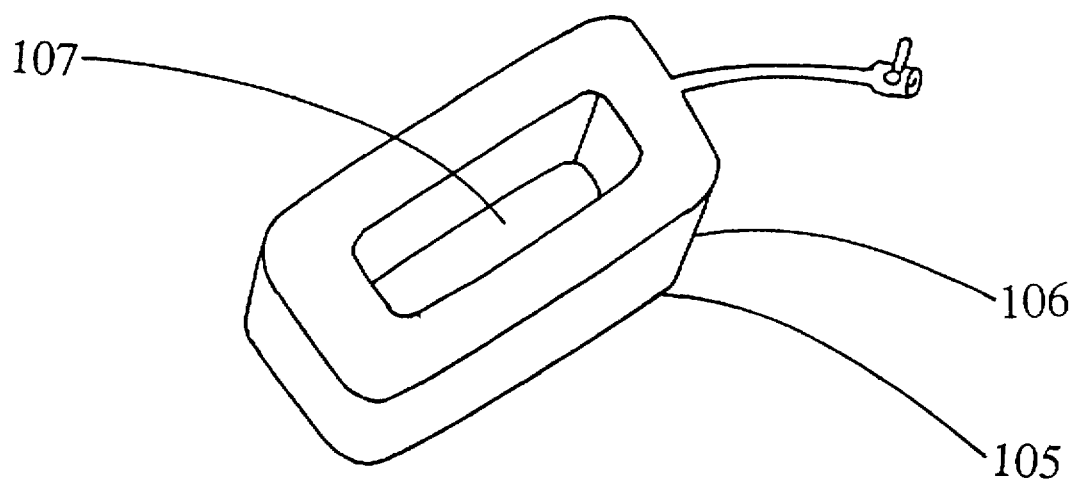

FIG. 16. Show a thick balloon with an opening in the body.

Figure 17:
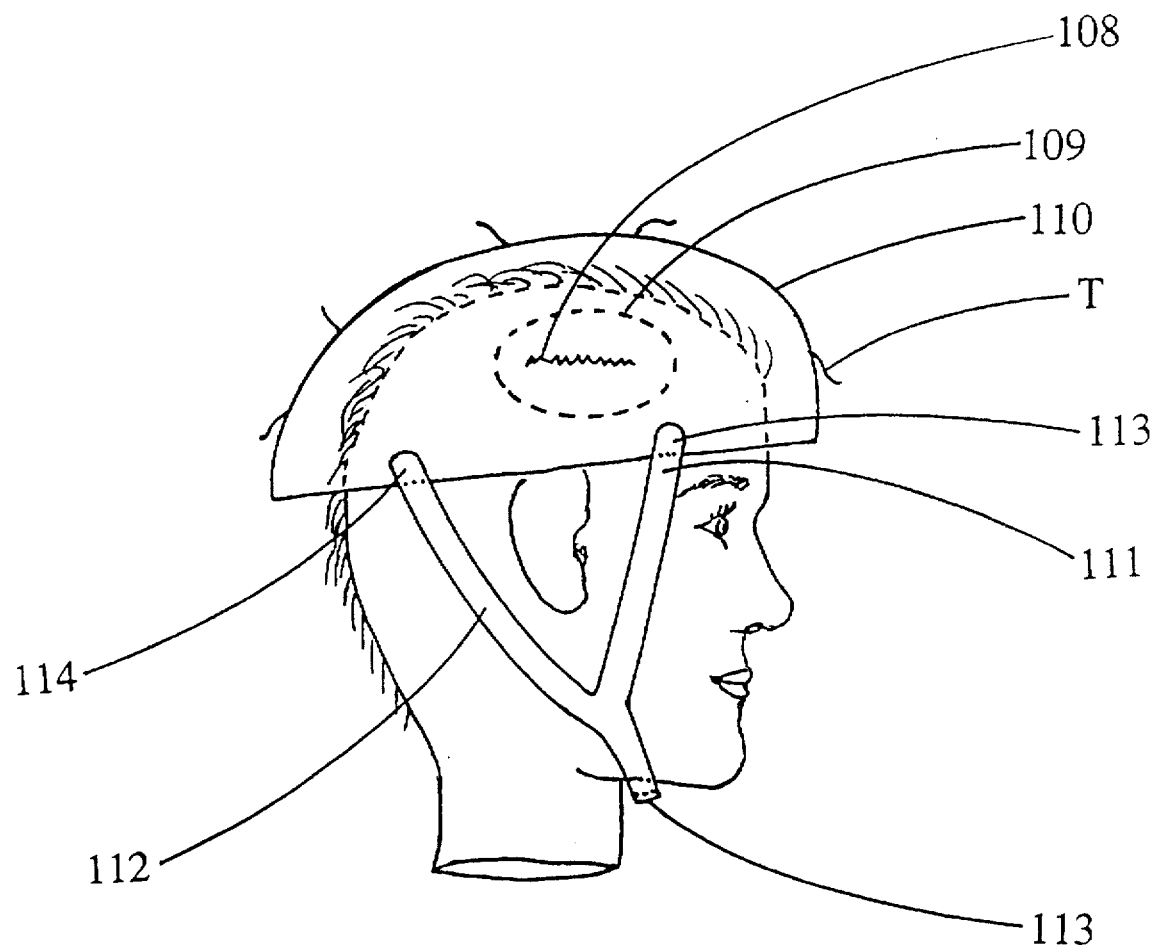

FIG. 17. Shows a dome-shaped support unit to fit certain areas such as the patient's head.

Figure 18:
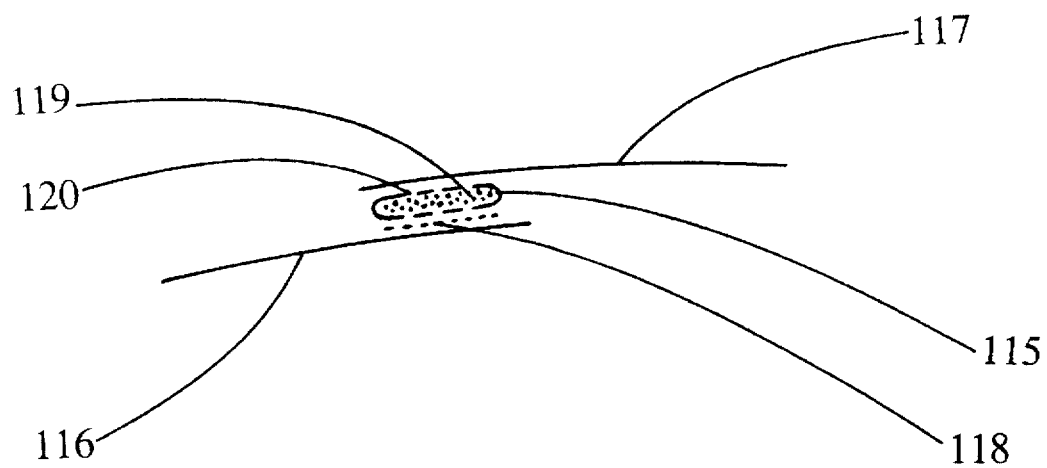

FIG. 18. Shows a special adhesive mean designed to allow certain pieces of these units to be adhered to each other.

Figure 19:
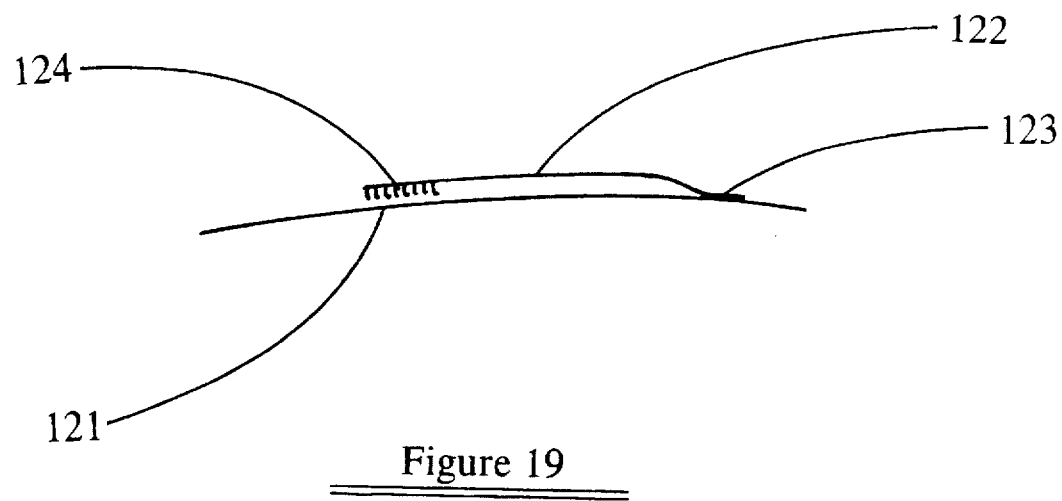

FIG. 19. Shows a unit that allows the length of the strap to be adjusted.

Figure 20:
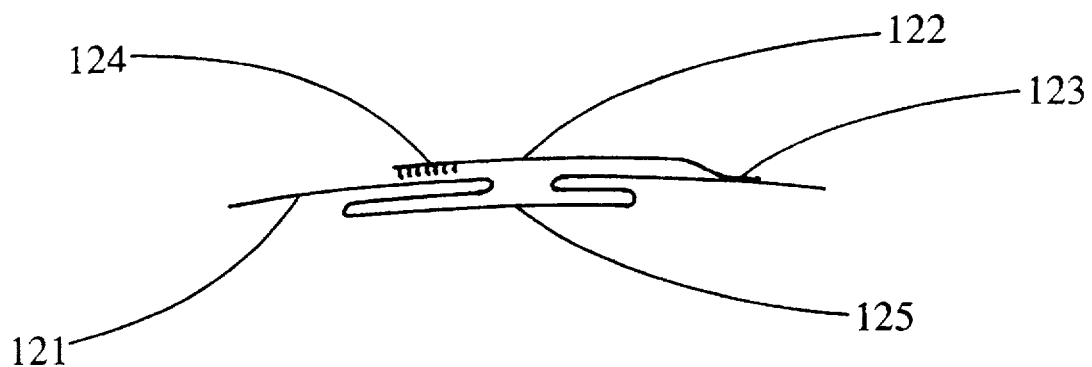

FIG. 20. Shows how the strap in FIG. 19 will function.

DETAILED EXPLANATION OF THE FIGURES

FIG. 1. Shows the general appearance of a patient who has a unit 1 on his body in the right upper quadrant over an incision site 12 which is due to gallbladder surgery. This unit may be used in many other areas such as after breast procedures. The body of the patient is shown in a dotted line and the body of the support unit at 1. This particular unit has three end pieces such as 2, 3 and 4. The wound site is shown at 12 and the gauze pad at 11. This support unit is held in place by the strap means which are connected to its end pieces by an adjustable and reversible means. These straps are designed to go around the body in order to hold the unit in place securely. One strap shown at 5 goes around the trunk and will have its end pieces 6 and 7 to connect to the end pieces 4 and 3 from the support unit respectively. The unit also has another strap 8 which has a rear end that connects to the rear part of the trunk strap 5 in the back; its front end piece shown at 9 will connect to the upper end piece of the support unit shown at 2. The unit may also have a fourth strap that may come from the left shoulder area to connect to the strap 5 in front and back. The function of the straps are as follows:

a. The horizontal trunk strap will function to hold the unit in the area and prevent it from moving horizontally.

b. The strap 8 will prevent the horizontal strap from moving vertically to fall below the wound area.

c. The unit may have another strap to prevent the horizontal strap from moving vertically.

The length of these straps will be adjustable in order to allow proper sizing to be chosen. Basically, the straps will be non-stretchable units although in some models they may be made to be elastic or may have some elastic components or segments in their body. This will be more true in cases in which the straps are to pull the support unit toward the wound and such a wound does not need the compression units such as inflatable balloons. Importantly, the shape of the support unit may vary and in some models such as the one shown at FIG. 12 the end pieces may be made to be in the corners of a rather regular triangle, in order to allow even pulling of the center of the support and a rather equal pressure to the center. No 10 shows a pocket which is to hold the suction bulb, drainage tubing and things of that nature that would be better to be held in the area more conveniently and securely to prevent them from wandering around, causing concern, or from being pulled out accidentally. This pocket has the opening 10A which may have a purse string type opening to hold the tubings inside even more safely. Please notice that although this pocket is shown only in this FIG., the other models may also have the same part or a modified part as well. Importantly, the unit may also have bands of adhesives that will be used to connect the support unit to the skin as well. This will be more true in cases which have a frame and door mean as the support unit when the frame is to be held in place securely and the door or the second cover will be the access area.

Please notice that although this unit is shown to be used on the left side, it may be modified slightly to be used on the right side as well. And it may also be used on other parts of the chest as well.

FIG. 2. Shows schematically the general view of a unit that is designed to be used after surgeries in the center of the body and its vicinity such as open heart surgery or any other areas where this unit will be useful. Basically, this FIG. also shows a rather rectangular shaped body of the support unit at 13 which is standing over the wound site 14 and the gauze pad at 15. This particular unit has six end pieces such as 16, 17, 18, 19, 20 and 21. This support unit is also held in place by the use of strap means which are connected to its end pieces by adjustable and reversible means. One pair of these straps shown at 23 and 28 will go around the body and the unit also has the straps 26 and 27. From one side these are connected to the rear part of the strap 23 and may even be connected to the body of the strap 28 and from the other side their end pieces will connect to the end pieces 16 and 17 from the support unit. The length of these straps will be adjustable.

FIG. 3. Schematically shows a unit which is similar to the unit shown in the previous FIG. 2. Except the unit In this FIG. has a band of connection mean on its border as shown at 30 which is made from a connection mean such as Velcro (™) hook so that this design allows the straps to be connected to this band in any convenient or more efficient spot, which will give significant freedom of choices in this regard. In this FIG. the border to the central piece is shown at 29 and the outer edge of the Velcro (™) band at 30 the wound at 14 and gauze pad at 15. One pair of these straps shown at A and B will go around the body and the unit also has straps C and D. From one side these are connected to the rear part of the strap A and may even be connected to the body of the strap B and from the other side their end pieces will connect to the continuation of the connection band of the unit shown at 30. The end pieces of the strap A marked at E and F as well as the end pieces of the strap B marked at G and H will connect to the continuation of the connection band of the unit shown at 30. Importantly, the nature of the adhesive connection mean band in the border of the support piece may vary. It may be made to be from a layer of adhesive that will be protected by a cover that will be peeled off before use. The cover may have a series of cuts in order to allow only one part of the adhesive to be uncovered. Instead of the band the unit may also have patches or segments of adhesives areas on it that will be covered by a protective layers. Importantly, other means such as snaps or similar units may be also used for such a purpose.

FIG. 4. Schematically shows the front view of a unit which is similar to the one shown in the previous FIG. 1 except this unit has a door that allows it to be opened, the wound site to be accessed and the wound dressing to be checked. Importantly, this design allows the wound site to be approached without the need to dismantle the whole unit. The applicant has a patent for this model; here, a model of such a unit is shown that has three end pieces and is particularly made for the upper lateral chest procedures such as the breasts or pacemaker cases. The door may hold the gauze pad in place and the pad of gauze may be surrounded by a flexible thin vinyl wall in order to prevent the secretions from contaminating the door and the area. In some models the rear side and the sides of the gauze pad may have impermeable materials to prevent contamination of the surroundings with the materials from the gauze. In this FIG. the body of the clear, front support piece is shown at 31 and its three end pieces at 32, 33 and 34. The end pieces have patches of Velcro (™) for the connection means. The unit also has a clear door 35 marked by a dot-dash line that is hinged to body of the front piece by the hinges means 36 so that the door can be opened along the hinges. Importantly, this door has the frame 35A which may be made from a rather rigid material in order to give a body or skeleton to the door in order to be functional. This frame may have a pre-designed shape or it may be made to be shapeable (with use of pieces such as aluminium) in order to allow its shape to be modified to accept a given shape to function more suitably. The snap mean 37 will allow the door to be kept in a closed position. The support unit may also have a rectangular frame marked at 38 which will further support the door. The unit will support any materials that are needed to be used on the wound site, such as gauze pads, the inflatable, transparent balloons, etc. The consistency of the frame, the door, the support may all vary; they may be made to be rigid with special shape, curvature and contour in order to allow the unit to fit the anatomy of the area well. Or they may have a shapeable body to allow their contour to be modified to match the shape of the area. Importantly, the size of the door may be bigger than the opening of the support, and the door may be a cover in order to allow a unit in the center to be held in place securely which at times may not be done by use of a small door. This is shown in FIG. 4A.

FIG. 4A. Schematically shows the front view of a support unit which is similar to the one shown in the previous FIG. 4 except this unit has a larger door marked at 35B which allows the door to act like a larger cover over the opening of the unit in order to provide a more secure closure. In this FIG. the opening of the unit has the frame shown at 38A and the door 35B is connected to the body of this unit along a long hinge mean 36A which will allow it to be opened along this line; the door also has a tab 35C which will allow the door to be moved conveniently and the snap means 37A and 37B will allow the door to be held in a closed position. Importantly, the nature, number and other important characteristics of these snaps and the whole unit may vary. The reason for having a door or a cover is that the process of dismantling the whole unit, disconnection of the straps from the support unit, and connecting them back is not easy each time and every place. The straps will drop down or move to the side to make the re-connection a time consuming job. For this reason, this applicant introduces such models that will allow the main body of the unit which may be only a frame or skeleton to be kept in place and only to open the door or the second cover. The process of keeping the door closed on the body of the support unit may use many connection means that can be of any kind including the Velcro (™) patches. The hinge mean may be just sewing or attaching the body of the door on the wall of the support unit. Since the body of the door is flexible, it will automatically function as a hinge mean.

FIG. 5. Shows the front view of a gauze pad that is designed to hold the secretions inside and prevent outward movement and dripping of the secretions. This is made from a gauze pad 42 that is caged inside a layer of thin, transparent, non-permeable plastic 39 which goes around it.

This cover also has a curved rim or a wall 40 attached to its rim 39 so that it will make a pocket 46 inside (shown at FIG. 6) that will prevent the secretions from passing to the surrounding areas from a contaminated gauze pad and to drip in the dependent areas. This unit will have the advantage that it will not contaminate the surrounding areas such as the support unit shown here in FIG. 1, 2, 3 and 4. This method will allow the gauze pads to be placed on the wound site easily and under this support unit and then to be replaced by a new one easily. No 43 show the border of the short left side wall; the body of the cover may have a small tab 44 in order to allow the unit to be held and moved easily.

FIG. 6. Shows the cross cut view of the gauze pad shown in the previous FIG. 5. In this view the lower body of the non-permeable body is shown at 45 and its rim on the right side is marked at 39, the edge of the short wall is marked at 40 and is attached to the body at rim 39; this design makes the pocket 46 in between them. The tip of the short wall at the left side is marked at 43. The gauze pad is shown 41 with its front wall marked at 47 and its rear wall at 48; the tab 44 in shown in the left side. Importantly, the size, shape, thickness, relative sizes, and all the other important characteristics of these units will vary in different models.

FIG. 7. Shows a patient who is wearing a unit similar to the unit shown in the FIG. 1 on her body except this unit also is holding an inflatable balloon on the breast wound site to prevent bleeding and oozing secretions. In this view the body of the person is shown at dotted line, the left arm at LA and the right arm at RA; the left breast is shown at LB. The applicant apologizes that the Fig is a crowded Fig but in order to understand this FIG. better please first review the FIG. 8 which will help to understand this FIG. easier and better. In this FIG. the body of the support unit at 49 has three corners as marked at 53, 54 and 55. The unit has a clear balloon marked at 50 which has the inflation port 52 for its inflation. The front of the balloon has a small, transparent, semi-rigid or rigid wound piece marked at 51 which is over the wound marked at X which is hardly visible. This unit is held in place by the strap means connected to its end pieces by adjustable and reversible means. These straps are designed to go around the body in order to hold the unit in place securely. One strap goes around the chest and wraps the chest to have its end pieces K and L to connect to the end pieces 55 and 54 from the support unit respectively. The unit also has another strap I whose rear end will be connected to the chest strap in the back of the chest and its front end piece shown at I will connect to the upper end piece of the support unit shown at 53. The unit may also have a fourth strap L that will have its rear end connected to the chest strap in the back of the chest and its front end shown at L will connect adjustably to the front piece of the chest strap at point M. The function of the straps are as follows:

a. The chest strap will function to hold the unit in the area and prevent it from moving horizontally.

b. The strap I will prevent the chest strap from moving vertically to fall below the wound area.

c. The strap L will also prevent the chest strap from moving vertically.

The lengths of these straps will be adjustable in order to allow proper sizing to be chosen.

The straps will be non-stretchable although they may have a somewhat elastic body or some elastic components or segments in their body.

Importantly, the shape of the unit may vary and the lower end pieces may be made to be in a somewhat triangular shape to hold the balloon more securely.

Please notice that although this unit is shown to be used on the left side, it may be modified slightly to be used on the right side as well. And it may also be used in the other parts of the chest as well.

FIG. 8. Shows schematically a larger view of the unit shown in the previous FIG. 7. This unit is designed to be used particularly in the procedures that are done in one side of the body such as the breast procedures. This FIG. shows the body of the support unit at 49 which has three corners as marked at 53, 54 and 55. The unit has a clear balloon marked at 50 which has the inflation port 52 for its inflation. The front of the balloon has a small, transparent, semi-rigid or rigid wound piece marked at 51 which is over the wound marked at X which is hardly visible. This unit is held in place by the strap means connected to its end pieces by adjustable and reversible means. These straps are designed to go around the body in order to hold the unit in place securely. One strap goes around the chest and wraps the chest to have its end pieces K and L to connect to the end pieces 55 and 54 from the support unit respectively. The unit also has another strap I that has its rear end connected to the chest strap in the back of the chest and its front end piece shown at I will connect to the upper end piece of the support unit shown at 53. This unit will be held in place by a strap means that will be connected to the end pieces of the support unit by adjustable and reversible means. Here, in this model, the connection means area is chosen to be Velcro (™) patches. These straps are designed to go around the body in order to hold the unit in place securely. One strap goes around the chest and wraps the chest to have its end pieces J and K to connect to the end pieces of 54 and 55 from the support unit respectively. These straps will be made from the loop kind of the Velcro (™) or they may have end pieces which has Velcro (™) patches on them to allow them to be attached to the matching parts of the end pieces 54 and 55 from the support unit. The unit will also have another strap I that will have its rear end connected to the chest strap in the back of the chest and the front end of it shown at I will connect to the upper end piece of the support unit shown at 53. The unit may also have a fourth strap L that will have its rear end connected to the chest strap in the back of the chest and the front end of it shown at L will connect adjustably to the front piece of the chest strap at point M.

The length of these straps will be adjustable. This support system will be a stable unit to hold an inflatable balloon in the area in order to compress the wound site.

The front of the balloon may have a rather small, clear, rigid wound piece that will allow better compression of the wound site. The size, the consistency of this piece will vary and its contour may also vary as well, so that it will allow a proper and desired impression to be made on the wound area. For example, in the breast area a rather concave shape may be desired, however in the case of permanent pacemaker insertion the shape of the unit may be chosen to match the shape of the pacemaker and the wound site. This will be also true in other cases and wounds as well.

The support unit may also have a clear, semi rigid or rigid piece in its front located between the rear surface of the body of the support unit and the front surface of the balloon in order to allow better positioning. In some models the rigid piece may be used to give a body and a particular shape to the support unit. Also, in some models the rigid piece may have some parts or pieces that will be more flexible and will accept and hold a modified shape in order to allow the shape of the unit to be modified to match the shape of the area and wound site. These pieces will be similar to an aluminium sheet that will hold the given shape.

FIG. 9. Schematically shows a cross-cut view of the unit shown in the previous FIG. 8. In this FIG. the body of the clear, front support piece is shown at 49 and the cross-cut view of the end pieces 54 and 55 which are covered by a patch of Velcro (™) hook. The unit is supporting an inflatable balloon shown at 50. The balloon has two walls, the upper wall 56 which is attached to the lower surface of the support piece 49 by the adhesive patch 58. This connection can be reversible or permanent. The reversible cases of the unit will allow differently sized or shaped balloons to be used with the support unit. The lower surface of the lower wall of the balloon marked at 57 is connected to a small, clear, rigid wound piece 51 by a reversible or a permanent adhesive means 59. In this case, also, the reversible attachments will allow a differently sized or shaped wound (front) pieces to be connected to this unit. The tubing of the balloon is shown at 60 and the inflation port of the balloon is shown at 61. The port has a valve means here marked at 62 that will close the opening of the port.

The balloon of this unit will be connected to a hand-held inflation unit which will allow it to be inflated and a pressure gauge will be used to monitor the pressure inside the balloon.

Importantly, the shape of the balloon may vary: the unit may be made to have a bulging balloon similar to the one shown at 66 on FIG. 10 so that instead of the flat balloon this unit will have a bulging balloon in its front. This balloon will be supported by the front support piece.

FIG. 10. Shows a particular model of these units which is of special interest and is made from combining a domed balloon such as the one shown at 66 to the unit shown at FIGS. 7 and 8 so that instead of the flat balloon these units will have a bulging balloon such as the one shown at 66 in their front. Basically, this will be a unit very similar to the unit shown at FIG. 9 except the support unit shown at 63 supports a bulging balloon shown at 66. This model will also have a support piece made from a non-stretchable support piece 63 which is very similar to the support unit shown at FIG. 7 and 8. It will have end pieces similar to 53, 54 and 55. This support unit will have a bulging balloon 66 in its front. This balloon will be a unit that will basically have a flat, rear surface and a rather bulged front surface; it will mostly expand forward. This balloon may be made to be either part of the unit or it may be attached to the support unit on a reversible or a permanent basis. This balloon may also have other parts such as the wound piece in its front. This balloon like the other balloons may also have a layer of adhesive in its front to allow it to adhere to the wound to the wound piece or to allow other pieces such as a gauze pad to be attached to it. The balloon may also have a pad of gauze attached to its front as well. The wound piece may be attached to the front of this balloon on a detachable or on a permanent basis. This allows the pressure or the compression of unit to be directed and applied to the wound site. The rear part of the balloon in the support area may also have a transparent rigid piece in order to allow most of the expansion and pressure to be applied forward toward the wound site.

FIG. 11. Schematically shows the front view of a unit which is similar to the one shown in the previous FIG. 4 except in this unit the door has a balloon inside it and attached to is so that this method will allow the door to be opened and the wound dressing to be checked. The front of the balloon may also have a pad of gauze that will be used to absorb materials. The balloon may be removably attached to the door. This unit has a frame shown at 73 which may be made from a rather rigid material to hold the door securely. This unit is designed for cases such as the state after an operation when wound care is more likely to be long term.

The front of the balloon may also have a pad of gauze to absorb secretions. The rear surface and the sides of the gauze pad may have an impermeable material to prevent contamination of the surroundings with material from the gauze. In this FIG., the body of the transparent, front support piece is shown at 69 and its three corners at 70, 71 and 72. The end pieces have patches of Velcro (™) for connection means. The rectangular frame is marked at 73 which has a clear door 74 marked by a dot-dash line hinged to it by the hinge means 75 so that the door can be opened along the hinges. The snap mean 76 will allow the door to be kept in a closed position. The unit supports the inflatable, transparent balloon 77 shown by a dashed line that will be properly sized and shaped to compress the wound site. The balloon has the inflation port 78 which allows the balloon to be inflated and the inflation port has a valve mean (not marked) that will allow it to be closed. The consistency of the frame, the door, and all other important characteristics of this support unit may all vary; they may be made to be rigid with a special shape, curvature and contour in order to allow the unit to fit the anatomy of the area well.

Importantly, the frame may have a unit of balloon in it in order to allow the sides of the incision site to be compressed; the front surface of the balloon of the frame may also have a rigid wall on it in order to allow a rather flat type of compression to be made. This frame may be also made from a material such as aluminium that will allow the shape and contour of the piece to be modified as well, the flat part on the front of the balloon may also be made to hold a given shape. Importantly, the front of the wall of the border of the balloon may also have a layer of gauze in order to absorb fluids such as sweat in the area and to make it more comfortable and less irritant to the skin.

FIG. 12. Schematically shows the front view of a unit which is similar to the one shown in the previous FIG. 8 except firstly the body of the support has a rather larger area and secondly the corners of this unit are placed in a different axis in order to allow the balloon to be more secure in these cases. This is like having the attachment corners 80, 81, 82 of the support unit to be in the corners of a triangle. This FIG. also shows the wound piece 84 which will be a rather small, transparent, rigid wound piece that will allow better compression of the wound site. As mentioned earlier, the size, shape, consistency and other important characteristics of this unit and the wound piece will vary in order to allow the proper impression to be made on the wound area. As mentioned above, for example, in the breast area a rather concave shape may be desired; however, in the case of the wound of a permanent pacemaker insertion, the shape of the unit may be chosen to match the shape of the pacemaker body. This unit has a door that holds a balloon inside it and attached to it so that this method will allow the door to be opened and the wound dressing to be checked. The wound piece may also have a piece of gauze connected to it on a reversible basis in order to absorb secretions; the gauze pad may be exchanged to allow a new one to be attached to the front of the wound piece. No 85 shows a piece of transparent, rigid, plastic piece shown at dots and dashes which will be placed between the front lower surface of the support unit and the upper surface of the inflatable balloon. This piece is to allow the support unit to have a rigid body in order to hold certain compression units and, in this case, to prevent the rear wall of the balloon from bulging out. This piece may be reversibly connected to the support by adhesive means or it may be made to be a permanent part of the body of the support unit. The size, shape, thickness, consistency and other important factors of this piece may vary. The end pieces of this unit will have means of attachments to allow the straps to be adjustably connected to these means. These can be of any kind; however, in this model they are chosen to be patches of Velcro (™).

FIG. 13. Shows the cross-cut view of a unit designed to give a signal if bleeding occurs in the wound site. This unit is basically made from a gauze pad 91 which has sensor leads M and N inside; these will cause an electrical circuit to be activated if bleeding occur and the blood reaches the space between the electrodes inside the gauze pad. In this condition the presence of the blood between the electrodes M and N and due to its physical or chemical nature will cause the electricity to pass through the space between the electrodes to make the electrical circuit complete and set off an alarm or a signal. This gauze pad is covered by a clear, impermeable layer 86 that has a rim or border 87 and 88 which goes all around the gauze pad and is covered by a film of adhesive shown at 89 and 90. The band of adhesive will cause this unit to be attached and adhered to the skin around the wound and seal the area. In some models the front surface of the gauze pad may also have an adhesive film 92 on it, so that it will allow the gauze pad to adhere and seal the skin, make the unit stand in the area more securely, and keep the skin tight to prevent bleeding as well. The adhesive film will have openings or mini holes in it to allow blood from going through to reach the sensor leads. This method will allow the electrical circuit per-se or after amplification and alteration to cause different functions. These functions may consist of an alarm sounding, a signal to act or any other pre-designed actions or functions to be taken by the use of different systems such as mini computers, computers, and the use of different mechanical means such as air pumps, etc. In this Figure the cover of this unit is marked at 86 and the gauze pad at 91, the cross cuts of the circular sensors are marked at M and N.

FIG. 14. Is schematic FIG. to show how the bleeding detection system will function.

In this Figure the upper electrode M is shown and is a larger piece that goes over the lower electrode N, here shown with a dashed line. The center of the unit (shown at area 86) may be open to allow the color of the gauze pad to be seen. In the case of bleeding, blood will be absorbed by the gauze pad and will enter the space or area between the sensor electrodes M & N. These electrodes are connected by an electrical connection means or wires to a programmable, mini computer symbolically shown at 93 which will analyze the signals and may amplify or alter them in order to start a set of pre-designed actions to occur, such as causing an alarm to sound, informing the patient of any instructions to follow, and other actions such as activating an electrical pump to inflate a balloon, etc. In this Figure the electrode M and N are shown, the mini computer is marked at 93, the alarm inside it is symbolically shown at 94 and the battery is symbolically shown at 95. This system may also use a bed side button or a control unit so that an informed patient can press the button or use the control unit in order to inflate the balloon and apply pressure. The patient may also use the control unit as a way of relaying information to the medical staff as well as informing the nursing station via a proper network.

Importantly, the gauze between the electrodes may be treated with certain chemicals or materials in order to influence, exaggerate or modify the effect of the blood in the area for better chemical, electrical or physical detection. Also, in different models these chemicals may be changed to allow different secretions to be identified such as secretions from the wound, amniotic fluids, etc. The sensor method may also differ: it may use any sensors (physical, chemical or optical) in order to identify or modify the signals.

FIG. 15. is a schematic Figure which shows a unit similar to the one shown in the previous FIG. 13 and 14 which is removably attached to any of the support or compression units. This unit allows compression of the wound as well as detection of bleeding. This unit shows a compression unit shown at 96 with its balloon at 97 and inflation tubing at 98. The unit has the gauze pad 103 which has the sensor electrodes of 99 and 100 in it. The lower sensor lead has an opening 101 that will allow the blood to move into the gauze pad; the unit has an impermeable layer 102 that will not allow sweat to be absorbed by the gauze pad. Also, the unit has a layer of adhesive film shown at 104 that will allow the gauze pad to adhere to the wound site.

FIG. 16. Is chosen to show a few important characteristics of some models of the balloons. This unit shows how the balloon may have an opening 107 in the center in order to spare one area from being compressed and the things to go through. Secondly, it also shows that a unit such as the one shown at 105 can have a thickness shown at 106. Importantly, the size, thickness, configuration and all other important characteristics of these balloon may vary to allow different models to be made.

FIG. 17. Schematically shows a unit designed to have a dome shape in order to fit areas such as the patient's head in order to allow different wound care units such as gauze pads, compression units, etc., to be held in place securely. In practice, this is an area where it is difficult to use adhesive tapes and even to wrap. However, this design not only will allow the wound care units to stand on the area securely, but it will also allow the wound site to be visualized and pressure to be applied if needed.

In this FIG. the wound is shown at 108 and the gauze on the wound at 109. The support unit is shown at 110 and it is a transparent unit. This unit is held in place by the use of straps 111 and 112 which can be attached to it on a reversible or permanent basis on the sides of the support unit at 113 and 114. The straps may get together to attach the piece from the other site at 113A. This unit also shows a series of tabs marked at T which are designed to allow those to be held in order to allow the body of the unit to be moved or adjusted. These will be quite helpful in certain cases when circumstances will not allow the unit to be moved.

FIG. 18. Schematically shows a special adhesive mean that is designed to allow certain pieces of these units to be adhered to each other. This unit which was previously mentioned in the D. Devices is designed to allow attachment of the units when needed. This unit is basically made from a special small envelope, chamber or a container mean (here referred to as "the envelope") that holds a specific amount of the adhesive material inside. This unit will be used between two pieces and compressed so that the adhesive material will be squeezed to leave the envelope and to allow the attachment. In this FIG. the body of two pieces that are to be attached to each other is shown at 116 and 117; the envelope is shown at 115. The envelope is attached to the body of one unit 116 by the use of the adhering mean 118 so that it will be conveniently attached to the piece 116 and ready to be used when needed. The body of the envelope has multiple micro-perforation means such as the one shown at 120 that will be functional only when they are squeezed with a pre-designed pressure. Then they will open to release the adhesive material here shown at 119 so that it will allow the two opposing units to be stuck to each other. This will make a convenient way of adhering two pieces to each other on an optional basis.

FIG. 19. Shows schematically a special strap that has a body that allows the length of the strap to be adjusted easily. The body of this strap shown at 121 is made from a Velcro (™) loop and it has other shorter pieces of strap shown at 122 which is fixed to the body of the strap 121 at point 123. The strap 122 has a piece of Velcro (™) hook in its end as shown at 124. This construction will allow the piece 124 to be removed to attach further on the body of the strap 121 to shorten its length as desired as shown in FIG. 20.

FIG. 20. Shows schematically a strap unit that is very similar to the unit shown in the previous FIG. 19. Except in this Figure the piece 124 from the strap is to be attached further on the body of the strap 121 and this has allowed a segment of strap 121 as shown at 125 to be removed from function and to shorten its length. This method allows significantly changing the length of the strap. This method will be more useful in cases such as a long chest or trunk straps that may need to shorten significantly to fit a smaller sized person.

The nature of these pieces may be different in different straps. For example, the body of strap 121 may be made from vinyl and the piece 124 may be made from a film of adhesive protected by a removeable layer that will be peeled off at the time of use.

Alternatively, the strap 121 may be made from a Velcro (™) loop and the strap 122 from Velcro (™) hook. This can be simply stuck on to the body of the strap 121 in different areas.

DETAILED EXPLANATION OF THIS INVENTION

Wound care and prevention of bleeding in the body of humans or animals are of special importance and should be done carefully and properly. Any wounds such as cuts, surgical wounds or any other procedural or therapeutic wounds should be properly dressed in order to prevent bleeding, swelling of the tissue, infection in the area, and other contaminations, etc. This is a very big issue in the practice of medicine. Commonly, these wounds (the "wound" implies all of the wounds and cuts, etc., in this application) are covered by gauze pads which are held in place and sometimes compressed by the use of adhesive tapes, or they will be held in the area by a bandage or wrap that goes around the body at the wound site. However, these methods have many disadvantages and problems: adhesive tapes and adhesive materials cause skin reactions, pain and discomfort while being removed, and they simply do not stick well when the area is covered by hair. Many times the area needs to be shaved which is a process on its own and needs further expense and energy. Holding dressing on an area such as the scalp is not easily and is problematic in practice; also, the adhesive taping is both difficult and ineffective. On the other hand, wrapping the wrapping materials around the wound is not easy, either. The process is difficult since the patient has to sit up or move up and the surrounding area of the wound has to be clear for this process to be completed. This takes significant time and energy which should not be spent if possible. Furthermore, when there is a need for compression of the wound the above mentioned methods simply can not apply enough pressure to the wound site to control heavy bleeding such as arterial bleeding. Such pressure can not be measured, increased or adjusted. This method also does not allow the wound site to be seen, and changing the dressing has to be done by repeating the dressing and doubling or tripling the above mentioned problems. For those reasons this applicant has previously introduced units to solve similar problems and contribute to humanity and work for a better human life. His previous applications such as D. Device. Pressure Bandages and Dressings. the Latex Support , D. Device 2. D. Device 3. D. Device 4. D. Device 5. D. Device 6. D. Device 7. Daneshvar's Device 8 and 9 are all related to these or similar problems. However, due to the unfamiliarity of the applicant with the procedure of the patent applications and the election requirements, many of the important aspects of those units could not be claimed in one application. Thus, he would like to introduce this unit which has its own new matters, important elements and teachings. it also stresses some important points of the previous embodiments.

Basically, this invention introduces a support unit that is primarily made from a flexible, stretchable or non-stretchable, transparent material such as vinyl which is shaped to match the shape and the anatomy of the area and to stand on the wound site properly.

This support unit has the following properties:

1. It may be made from a flexible, non-stretchable material such as vinyl which is shaped to match the shape and the anatomy of the area and to stand on the wound site properly.
2. The body of the unit may be made to be transparent or it may have a transparent window in order to allow the wound area under it to be seen.
3. It also may be made from a flexible, stretchable, material such as latex which basically will be shaped to match the shape and the anatomy of the area. However, the stretchable body will allow it to be pulled to fit the area even better and the pulling effect of the stretchable material will hold the unit in place more tightly and securely.
4. The support may have a window as shown in Fig in order to allow it to be opened for the wound care. This will make this process easy and simple.
5. The support may have a series of means of connections on it in order to allow bands or straps to be attached to it on a reversible or permanent basis. The connection means can be of any kind Velcro (™) patches, adhesive bands. D. rings, snaps and any other proper means of connections.
6. The support may have a border with means of connections on it in order to allow bands or straps to be attached to it on a reversible or permanent basis. Again, this can be of any kinds of connection means such as bands of Velcro (™), adhesive bands, a series of D. rings, a series of snaps or any other proper means of connections.
7. The shape of the unit may vary on a two-dimensional basis. It may be made to be round, oval, square, rectangle or any other shapes in order to fit the shape of the site of the wound best.
8. The shape of the unit may vary on a three-dimensional basis it may be made a concave or convex shape, etc., in order to allow it to be used in certain areas. For example, in the scalp area it would be best for the unit to have a dome-shaped body in order to fit the area better and to allow it to hold the materials more securely.
9. The unit may have different shapes, designs, coloring or marking on it in order to help the user to use them easily.
10. The thickness of the unit throughout may vary and in some areas the unit may be thicker than others.
11. The unit may have other parts such as pieces of clear, rigid shaped plastic connected to it in order to give a contour or a special shape to it.
12. The support unit may be altered to hold different kinds of compression units such as screw, lever, cylinder and other mechanical pressure units on it to allow it to be functional.
13. In some models, the body of the support unit may be made from a rigid material that will be shaped to fit the anatomy of the area best and be held in place by various means.
14. The support piece may also have a body that will allow the shape of the support system to be changed and adjusted: this can be achieved by having the body or some part of the body to be made from materials such as aluminium shielding that allows the shape to be modified.
15. The support units may have a hole or opening in its front in order to allow a tubing or other units to go through it.
16. This support units will also have a series of tabs with a sample shown at FIG. 17 at T which are designed to allow the body of the support units to be held, moved and adjusted. These tabs will be quite helpful in cases when circumstances will not allow the support unit to be moved.
17. The surface of the support in the patient's side may also have a patch, a band or bands of adhesive film protected by a layer of cover that will be peeled off before use. This layer will allow the unit to be adhered to the patient's skin for further stability. This part is not shown in the picture but is a part that may be used in some models.

It should be mentioned that although these units are mostly shown for the left side they may be used on the right side as well.

This support unit will be kept on the site by the use of a series of straps. This support unit will be used to hold different dressing materials such as gauze pads, suctioning units, compression units, or similar other therapeutic and/or diagnostic pieces or units in place securely. This support unit will have a series of end pieces such as the one shown at 2, 3 and 4 from FIG. 1., which are designed to be attached to bands or straps (in this application the "straps" will be used to indicates bands, straps and anything of that nature) to keep the unit in the wound site securely. The number and location and other important characteristics of these end pieces will vary. These pieces will allow the unit to be connected to a series of straps by an adjustable and detachable proper means. Alternatively, the support unit may have a band of connection mean such as a Velcro (™) patch around it (such as the one shown at no 30 FIG. 3) in order to allow the straps to be attached to it. This is very important since it will allow the straps to be connected to the support unit in any suitable spot that can be chosen. Importantly, the connection band can be of any other kinds such as adhesive bands covered by pieces of removeable protective layers that will be peeled off before use. This band may also be made from an area that will allow the end pieces of the straps which have adhesive means to be connected to them optionally. This model gives a significant versatility and freedom of choice to the unit so that the user will have the option of connecting the straps to any proper area rather than a particular pre-designed spot which may not turn out to be the best spot for connection. The straps are designed to go around the limb, part of the body or the trunk in order to hold the support piece in place securely. The straps may have connection pieces between them to allow them to be even more sturdy. Such a connection will be used when the straps are to hold a unit in front; then they will have connections between themselves in the back such as the connections of the ladies' bras. This support system will be a stable, transparent, secure unit to hold gauze pads, pressure units or similar diagnostic or therapeutic units in the area securely.

The applicant has introduced the use of doors with these units and they are shown in FIGS. 4 and 4A. The main reason for the use of such doors is to simplify the process of exchanging the dressing and the gauze pads. Since commonly the process of dismantling the whole unit, disconnection of the straps from the support unit, and re-connecting them back to the unit is not easy each time and every place, the straps will drop down or move to the side to make the re-connection a time consuming job. For this reason, this applicant introduces such models that will allow the main body of the unit which may be only a frame or skeleton to be kept in place, connected to the straps. The user only needs to open the door or the second cover to exchange the dressing. The process of keeping the door closed on the body of the support unit may use many connection means that can be of any kind including the snaps, locks, adhesives, adhesive tapes and the Velcro (™) patches. The hinge mean may be made by sewing, sticking or attaching the body of the door on the wall of the support unit by any means. Since the body of the door is flexible, it will automatically function as a hinge mean. The body of the support may have a frame or skeleton to give more body and proper shape to the unit. Also, the door may have a frame as well for the same purpose as well, to give a body or skeleton to the door in order to be functional. This frame may have a pre-designed shape or it may be made to be shapeable (with use of pieces such as aluminium) in order to allow its shape to be modified to accept a given shape to function more suitably. The snap mean may be of any kind. The frames may have different shape, thickness, consistency, sizes, etc. The unit will support any materials that are needed to be used on the wound site, such as gauze pads, inflatable, transparent balloons, etc. The consistency of the frame, the door, the support may all vary; they may be made to be rigid with special shape, curvature and contour in order to allow the unit to fit the anatomy of the area well. Or they may have a shapeable body to allow their contour to be modified to match the shape of the area. Importantly, the size of the door may be bigger than the opening of the support, and the door may be a cover in order to allow a unit in the center to be held in place securely which at times may not be done by the use of a small door. Some more details of these units are shown in FIGS. 4 and 4A. Although this is shown in these FIGS. but the basic idea may be used in any other unit shown or referred to in this application as well.

Importantly, such a support unit will also allow certain means of pressure application such as inflatable balloons, screws, levers, piston-operated or other kinds of mechanical units to be used for compressing the wound site and preventing bleeding. Specifically, the inflatable balloons are of special importance since they will allow the wound site to be compressed in order to prevent bleeding, wound swelling, etc. Transparent balloons and a transparent support unit will allow the area of the wound to be visualized easily. Some models of these support units may have a door to allow it to be opened for convenient wound care. The doors may also have a balloon on them to compress the wound. Importantly, these units may also use gauze pads with sensors designed to detect bleeding if it occurs. This consists of a gauze pad that has at least two electrical sensors that are connected to an electrical circuit which consists of at least an alarm. The bleeding will cause the gauze to be contaminated with blood; this will complete the electrical circuit and cause a series of signals such as an alarm to go off. This unit can be programed so that a computer will inflate the balloon by a pump automatically to compress the wound site, while initiating an action for the medical staff to respond. This computer operated unit will also allow a plan for pressure application to be followed.

This unit may also use other pieces such as certain rigid pieces that will be shaped to be placed in the vicinity of the joints in order to wrap them around the joint to immobilize the joint during the use of these units. They may also use U-shaped support units to prevent from the strangulating the limbs due to use of tight straps which may cause a tourniquet effect. These issues were both discussed in this applicant's previous applications.

The idea of detection of bleeding and automatic compression of the bleeding site is important especially in conditions in which the anticoagulants are on the board or the wound is large, etc., and the bleeding can be serious. In some cases such bleeding can occur later in the course of the care and at times at a wrong time such as the middle of the night, when both the patient and the staff may not recognize it on a timely basis due to many factors such tiredness, exhaustion, the sedative effect of medications, the darkness of the room, etc. This can be dangerous: the patient may lose a significant amount of blood and may even suffer from more severe problems such as shock, its consequences and death. This unit may be made to have the following functions by one unit:

I. This unit will allow the compression of the wound site to occur during the early phase after a diagnostic or procedural intervention.

II. This unit will allow a low-level compression of the wound site to be done during the late phase of the wound care when there is no acute bleeding but there is still a need for low level pressure application.

III. This unit may use a special gauze pad that will allow the bleeding to be detected and the medical staff to be notified so they can attend the patient urgently.

IV. This unit may also use a system which will allow high level compression of the wound site if there is evidence of bleeding during the late phase of the wound care.

Importantly, in some models, the support unit will have a door that will allow it to be opened and the dressing to be inserted inside and removed conveniently. This design is to prevent from dismantling the whole unit for exchanging the dressing so that this process will not only take less time, but will also be easy enough for less educated people to use it. The dressings will also be simplified and they will come in a pre-packaged, ready to use, condition so that the user will only remove the old one to replace it with the new unit. This will eliminate the whole job of removing adhesive tapes, opening the wrap and putting them back on again, etc. This process will especially be lifesaving in man-made or natural disasters of large magnitudes with scores of casualties that would need a tremendous care. This unit may have:

m. A balloon mean connected to the door to compress the wound.

n. A balloon mean connected to the inner borders of the frame around the door.

o. The dressing may have the shape of an insert that will be placed and exchanged. The door will hold this insert in place securely. The insert may have a body made from a pad of gauze or combinations of the balloon and the gauze pad around it. The rear surface and the sides of the gauze pad may have a impermeable material to prevent contamination of the surroundings with materials from the gauze.

Use of balloons with this unit.

This application primarily uses inflatable balloons as the mean of pressure production unit. Basically, the balloons will be made to be flat, transparent balloons. They will be sized and shaped to expand and fit the anatomy of the area. These balloons will allow pressure to be created for prevention of bleeding as well as prevention of the diffusion of the secretions from the wound and related complications. Since the anatomy of each area as well the size and shape of each wound are different, different sizes and kinds of balloons will be used with these units. And the characteristics of the balloons will vary; these balloons may have different sizes ranging from small bubbles to big balloon. The thickness (when inflated) of the balloons may vary throughout as well; they may be thick in the center, or in some other areas, or may have almost the same thickness throughout. The thickness of their wall may vary from unit to unit to match the needs of the area since some wounds would need more pressure. Importantly, the thickness and consistency of the wall of a given balloon may be different from one area to another of the same balloon. For example, a unit may have a thicker and harder rear surface than its front wall and/or the balloon may have a rigid area in its front to act as the wound piece.

Models of these balloons may be made to have a soft body which after expansion will assume the shape of the area, the wound site, and will fill the empty spaces. Other models will be made to have a pre-designed configuration that after inflation will assume a pre-designed shape to affect the wound area and provide a particular impression in the area. The balloons may be filled with air, gas or fluid. The shape of these balloons may vary. Mostly they will be made flat, to expand and to compress the wound. They may also be made to only bulge on one side like half of a globe or so as shown at 66 FIG. 10. In other models the balloons may be made to have the shape of a cylinder. The balloons will be connected to the front of the support unit on a temporary or permanent basis. These balloons or expansion units may be made to have one or more handles to allow them to be controlled from a distance. For further convenience they may also have a gauze pad attached to their front wall. Importantly, the balloons may have an opening in the center to allow them to be placed on a wound site that has another part of unit such as a vascular sheath or an IV line inside. A model may have an opening on its side like the shape of a horse shoe in order to allow them to be placed around the IV lines or vascular sheaths. The balloons may also have extensions in order to fit the space between the IV lines or vascular sheaths. Some balloons may have different thicknesses to allow them to be used in particular areas. Combinations of different shapes and sizes of the balloons can be of help in patients whose needs are different. As mentioned earlier, some other important models will be made with the use of soft balloons whose walls will allow them to assume the shape of the wound area and the different therapeutic or procedural units on the wound site. This construction will allow such a unit to be placed over the entrance spots of the sheaths into the skin so that it will allow this particular site to be pressed in order to prevent oozing of the blood. So that part of these balloons will be placed between the tubing and vascular sheaths in order to press the wound area between them and prevent bleeding. These units will be more useful in conditions such as post angioplasty state in which patients have anticoagulants in their system as well as the sheaths in place inside the vessels, which can cause oozing blood around them.

Importantly, the balloons with different shapes may be made by sticking the walls of these balloons together along different lines. The applicant has made such unit with oblique lines of connection for the units that stand on the groin line and bends when the persons bends his/her groin.

The balloons may be made from combinations of the balloons in order to allow different amounts of pressure to be applied to different parts of the wound and also to allow differential pressures to be applied to a wound site. The combinations of the balloons may also be used to protect one balloon from another if perforation occurs. In some models the balloons may be filled with fluids for different purposes as well as providing heat or cold to the wound site.

Importantly, these balloons may be connected to a pressure measuring device to allow the pressure inside to be known; in some models they will be pre-charged units which are inflated to a certain degree prior to use.

The balloons and their related wound pieces may have signs, signals, printed lines, shapes, configurations of any kind, or colors to provide information and facilitate their placement and use. Also importantly, a balloon may be caged inside a proper cover in order to give it a particular shape after inflation. This caging may be used to influence the size and shape of the balloon or for sterilization purposes.

The end piece of the inflation tubes of these balloons may have a male or female standard IV tubing connection piece to allow easy connection to a three-way stopcock or the inflation unit.

Some special characteristics of these balloons:

1. The balloons may have pre-designed shapes to match the shape of the wound area such as breasts, chest wall, subclavian area, wrist area, forearm, groin, etc.
2. The balloons may have one or more tubes for inflation and monitoring pressure.
3. The inflation tubings may go through a hole in the support unit to reach the surface for an easy handling.
4. Use of balloons or bags filled with liquid will give the chance to apply cold or heat in the area.
5. The balloons may be connected to the support unit by different reversible or permanent connection means such as adhesives, Velcro (™) patches, snaps, etc.
6. Combinations of the balloons may be used so that one area of the wound may be pressurized while the other area would not affected as much. This will allow two balloons to be used for one area and only one for another. This technique will allow different periods of different pressure application, which is important in certain cases such as groin units to allow the arterial and venous sheaths to be removed under different pressure.
7. Also, in some models the balloons may have compartments of their own or can be made from combinations of a series of balloons in separate form or combined inside one cover. These balloons may be pre-charged or inflatable; in this case they may have a common inflation port or may have different and independent inflation ports. Some of these balloons may be chosen to be pre-charged. Alternative inflation of these balloons may be done and will be useful in some cases. Also, selective inflation of such balloons may be used in certain occasions. For example: to prevent one area to be pressed constantly.
8. A particular model of these balloons may be made in the shape of a long rectangular balloon so that part of the balloon can be rolled over and taped on the rear side of the balloon in order to adjust its length and shape; this will be of special use in having the balloon's shape and size under control easily.

9. The balloons may be made in different shapes with having its front and rear wall stuck to each other along a line and having an opening along this line in order to allow the air to go through that opening to make it like two different balloons connected to each other along the connection line. Importantly, this model shows how different shaped balloons may be made by sticking the walls of these balloon in different shapes.

10. These balloons may have hard, clear, plastic pieces attached to the rear surface with one or more handles in the sides in order to allow the position of this unit to be modified, tilted and controlled easily.

11. The balloons may have the shape of a ring or doughnut in order to be placed on a wound that needs to be dressed through the hole of the rings or has a catheter or sheath connected to it which does not allow the regular balloon to be utilized.

12. A fluid or gel-filled balloons may be used with the above mentioned support units. In this model instead of inflatable balloons the unit will use a special precharged balloon filled with air, fluid or gel to assume the shape of the area and transmit the pressure and tightness on the wound area for support. This bag or the combinations of the bags may contain numbers of air-filled small squeeze-able plastic bubbles to function as a buffer to allow pressure to be saved/reserved to be dissipated later. These small bubbles may be held in proper position inside the bag by the use of a structure or screen made from plastic, which was shown in previous application.

Importantly, the bags that contain such air or fluids may have their own inner compartments and walls to be made from combinations of balloons in order to prevent from shifting fluid as well as preventing all the unit from going flat if one gets perforated.

13. Also, the balloons may have an air-filled, soft, small balloon along or connected to the inflation tubing in order to allow the pressure inside the balloon to be estimated.

These balloons will have an inflation tubing with a proper ending to allow commonly used inflation units to be utilized. The inflation port may have valves of different natures such as one-way valves or three-way stopcocks, etc., to allow the air motion to be controlled. More than one tubing may be connected to the balloon in order to allow the connection of a pressure gauge or a similar unit.

Also importantly, these bags or balloons may have an open area in their center in order to allow the inspection of the wound site. Thus, it would not be necessary to remove the whole unit to inspect the wound site all the time. A door may be connected to this so that it can be opened for direct inspection. The inner wall of the door may have a matching balloon to fit the area. Optionally, a small battery-operated light may be incorporated to allow better lighting of the wound area for better visualization. Also, a magnifying lens may be attached to the cover to allow the wound view to be magnified. FIG. 9 is chosen to show a model of the balloon which has an opening in its center in order to spare one area from being compressed. Secondly, it also shows that this unit 51 has a height 52 and the balloon may be made to have a thickness. Importantly, the size, thickness, configuration and all other important characteristics of these balloons may vary to allow different models to be made.

The straps, their construction and functions.

The straps may be made from any functional material; they may have an adjustable length. The connection mean at the end pieces may be of any kind; for example, it may have a D ring in order to allow the strap to go through, make a U turn, and to be connected to the rear surface of its own. This was shown previously in D. Device units. However, particularly in these units straps made from Velcro (™) loop in combination with end pieces that have Velcro (™) hooks have functioned very conveniently in this applicants models. Alternatively, the straps may be made from different materials and can have end pieces covered with the Velcro (™) hooks; the lengths of the straps will be adjustable.

Importantly, these units may have multiple straps as follows in order to secure the unit in the wound site and prevent it from moving and falling when the patient stands. These units may use the following pieces:

a. The unit may use at least one horizontal strap in order to go around the chest or trunk and to function to hold the unit in the area securely and tightly and to prevent it from moving from side to side.

b. The unit may use at least one shoulder strap which will connect to the rear part of the horizontal strap and will connect to at least one upper end of the support unit. This is to prevent from the vertical motion of the chest strap.

c. The unit may also have another shoulder strap which will connect to the rear part of the horizontal strap from one side and to the front of the horizontal strap on the other side of the trunk. This strap will also prevent the vertical motion of the chest strap.

d. The unit may also have a connection piece between the shoulder straps in the back in order to hold them more securely in the area.

e. The unit may even have a connection piece between the shoulder straps in the front in order to further hold them more securely in the area.

f. The unit may have multiple horizontal straps in order to further secure the unit in the area.

g. In some models the unit may use a strap which goes around the neck in order to have its ends to attach to the support unit or the horizontal strap to hold the support unit in place securely. This will replace the shoulder straps.

The lengths of these straps may be adjustable. The straps will be made from a nonstretchable material although straps made from elastic materials may be used in certain models in order to pull the front unit and to hold it securely and allow for easy access to the area. In some models the non-stretchable straps may have some elastic components or elastic segments in their body.

The length, width, thickness, consistency and all other important characteristics of these straps may vary.

The methods of adjustment of the length of the straps.

Any methods and techniques may be used to control the length of the straps; however, the applicant introduces two special methods which he believes are new and of special importance although he has introduced these methods in his previous applications.

1. These straps may use one or more of a special bubble or patch of adhesive which will then be attached to one spot of the straps and allow them to be placed on the other part such as the body of the support unit and be pressed in order to release the adhesive material and make the adherence possible. These units will be made with the use of these small bubbles which keep the adhesive material inside their thin bodies; these bodies will have a series of small holes to allow for leakage of the adhesive due to pressure or simply the body will rupture and release the adhesive materials into the space between the two layers and make them adhere to each other. This method will allow the extra length of the strap to be connected to its rear side as well and to allow an easy mean of control of this condition. The adhesive material may be kept inside other kinds of spaces such as tubes, between two layers etc., again to allow the adhesive to be released by local pressure. This can also be done by the use of a layer of liquid adhesive covered by a layer of plastic that has weak points so that squeezing it causes leakage of the adhesive from the weak spots to the area between the two connection spots. The applicant is very optimistic about the use of this method; he believes that this is a technique with many uses as well and he keeps his right to apply for this basic unit, per se.

2. The other method will use a shorter strap on the body of the main strap which will allow one part of the main strap to be folded and held ineffective to shorten its total length. A model of this was introduced before on Latex support and is shown here at FIGS. 19 and 20. FIG. 19 schematically shows a strap that has a body that allows the length of the strap to be adjusted easily. The body of this strap shown at 121 is made from a Velcro (™) loop and it has another shorter piece of strap shown at 122 which is fixed to the body of the strap 121 at point 123. The strap 122 has a piece of Velcro (™) hook in its end as shown at 124. This construction will allow the piece 124 to be removed to attach further onto the body of the strap 121 to shorten its length as desired as shown in FIG. 20. This shows how this strap will function. In this Figure the piece 124 from the strap is to attach further on the body of the strap 121 which allows a segment of strap 121 as shown at 125 to no longer function and shorten its length. This method allows a significant change in the length of this strap to be done easily. This method will be more useful in cases such as a long chest or trunk straps that may need to be shortened significantly to fit a smaller size person.

The nature of these pieces may be different in different straps. For example, the body of strap 121 may be made from vinyl and the piece 124 may be made from a film of adhesive protected by a removeable layer that will be peeled off at the time of use.

Alternatively, the strap 121 may be made from a Velcro (™) loop and the strap 122 from Velcro (™) hook; these can be simply stuck on to the body of the strap 121 in different areas.

Use of a compact model of these units.

One model of these units will be made to have a front piece made from elastic material such as latex which will either have straps made from an elastic material such as latex or it will be made from a non-elastic material that is attached to the sides of the front support unit so that this unit can be used on the wound site in order to hold and support a gauze pad or similar units in place. For the following reasons this applicant believes that such units will provide a significant amount of versatility and help to the users and will make the process of the wound care much simpler (these were discussed in more details in the application of "Latex Supports".

I. They will be easy to use and will need much less time to be placed on the wound site which is of tremendous importance in medical care.

II. They will decrease the need for use of adhesive tapes that are of significant importance since the straps will hold the unit in place.

III. They will make the process of changing the therapeutic wound pieces (such as gauze) much easier since the user can move the support and place the other dressing on the wound.

IV. The units allow adhesive tapes to be adhered to them in order to change the length or the tension of the units. This has the advantage that the adhesives will not be used on skin as much as otherwise would be used.

V. The process of application will be easier and the unit may allow a smaller number of hands and fingers necessary for the use of these units.

The use of transparent, rigid front pieces for the base of the balloons:

These support units may also use a piece of rigid, transparent plastic to be placed between the wall of the support unit and the rear surface of the balloon as shown at 85 FIG. 12. Alternatively, this may be attached to the front surface of the support unit or the rear surface of the balloon by a reversible or permanent mean. The function of this piece is as follows:

1. This piece will stand against the expansion of the balloon and bulging it out and it will allow the force generated by the balloon to be directed toward the wound site and press that area.

2. This piece may be used to provide a proper shape to the front of the support unit. It may be a flat piece or may be made to be a concave or convex piece or to be shaped in other forms based on the need or the area. A convex piece will push the vertex of the balloon forward toward the wound site even further. This will allow the balloon to be inflated to a lesser degree to function the same.

3. This piece may be used to allow the support unit to be held in the area more stable. In this case the rigid piece may be made to have a pre-designed shape in order to provide special shape and body to the support unit.

4. Also, in some models the rigid piece may have some parts or pieces that will be more flexible and will accept and hold the shape in order to allow the shape of the unit to be modified and to hold the new shape in order to match the shape of the area and wound site.

This rigid, front piece may be attached to the surface of the support unit which is toward the wound site or it may be attached to the surface of the balloon which will not stand on the wound by a reversible or permanent mean, such as adhesives, snaps, etc. In some cases it may be simply placed between the balloon and the support unit. Importantly, in some models this piece may be inserted into an envelope in the body of the support unit or it may be part of the support unit as well. The reversible methods gives the option so that the user can choose to remove these pieces. The reversible models will also allow different front pieces to be attached to the support unit or to the balloon. The front piece may have a rectangular, circular, oval or any other shapes and their size, thickness, contour and any other important characteristics may vary as well. Importantly, in some models the support piece may be made from a rigid unit; then naturally this piece will not be needed.

The use of special gauzes with these units.

This applicant has previously introduced the use of gauze pads that are surrounded by a thin non-permeable plastic to prevent the secretions from leaving the gauze pad. In this application he stresses the use of gauze pads (such as the one shown at FIGS. 5 and 6) that are covered by a layer of thin, transparent non-permeable plastic around them so that it will not only hold the gauze pad inside but it will also have a curved rim that will prevent the secretions from passing the surrounding of the gauze pad and to drip and to make the support unit contaminated. Such a gauze pad will allow them to be placed on the wound site easily, be kept securely by the support units, and then to be replaced by a new one easily. The body of the cover may have a small tab no 44 FIGS. 5 and 6 or a series of tabs in order to allow the unit to be held and manipulated easily. The applicant believes that this method will simplify the care of many wound sites significantly.

The wound pieces:

These units may use a piece of small, rigid, transparent wound pieces attached to them on a reversible or permanent basis. The use of such wound pieces is important since they will allow the pressure of the balloon or other compression means to be applied directly to the wound area and prevent from the creation of a dome-shaped balloon wall. The applicant believes that the dome-shaped compression of the flat wound sites area to better to be avoided in most of the cases to prevent a less effective and inferior pressure application which does not match the shape of the area. These pieces may be attached to the front of the compression units on a reversible basis so that the user will have the option of choosing to remove these pieces; some models may not even have this piece in their front. The reversible models will also allow different wound pieces to be attached to the balloons. The wound piece may have a rectangular, circular, oval or any other shapes and their sizes may vary as well. In prototype units of this applicant, a rectangular shaped piece of about 4–6 cm by 4–7 cm or so was used successfully. Importantly, a different size piece may be even attached to the surface of the existing piece for the following reasons:

a. The attachment of the second wound piece will allow to change the shape, size or contour of the previous wound piece.

b. The attachment of the second wound piece will allow the user to increase the thickness of the unit to compensate for the depth of the unit in certain cases. These wound pieces may use other connection means to attach themselves to the wall of the incoming unit besides the adhesive means. They may have a matching cradle in order to allow one to attached over the other.

Importantly, the wound pieces may have openings in their center or may be designed to shield or protect some parts or some areas of the wound or a medical piece in the wound site (such as the body of vascular sheaths) from the pressure of the balloon. These pieces may have different designs with different curves, domes or contours in order to perform such functions. Examples of such a front pieces are shown at 51 on FIG. 8, 51 on FIG. 9, at 67 on FIG. 10 and at 84 on FIG. 12.

Use of compression means with the support units.

Importantly, one important functions of these units is to aid in preventing bleeding and swelling of the wound site. One stage at which bleeding occurs after operation is the early phase after the operation since during this period the blood is not clotted yet and the tissue has not healed enough to prevent bleeding and oozing of the secretions. For this reason, this applicant advises the use of application of pressure to the wound site in this early stage of operation; this can be done easily by the use of these units. Although the balloon means are the primary means of compression, other compression means may be used as well. The support means of these units will function as the backbone to allow the following unit s to be used for the application of pressure on the wound site:

I. Primarily, the balloons will be used to apply pressure on the wound site.

II. A pad of gauze or similar means may also be used for the application of pressure as well.

III. The support unit may also be used for the application of pressure on the wound by the use of a force generated by spring means. In such cases a spring means will be used to press a balloon, wound piece or gauze pad on the wound site.

IV. The support system may allow a screw means to be used to move a pole forward to press the wound by the use of a wound plate or a gauze pad. The screw may be rotated manually, by an electric engine or any other means.

V. The support system may also be used to support a lever means for applying pressure on the wound site. This will be very much similar to the screw system mentioned above and will have a pole that will be pushed down toward the wound to press a wound plate.

VI. A combination of a screw/lever means may also be utilized to combine these two useful techniques in order to make a more effective unit that can be handled even more easily for this purpose.

VII. A hydraulic system means made from a piston and cylinder may be used alone or with a lever system to generate the force for the compression of the wound site. In this model the base of a cylinder will be mounted on the support unit so that the plunger from the cylinder will move forward to press a wound plate toward the wound.

VIII. This support unit may support a motor (electrical, spring powered, etc.) to push a pole forward toward the wound site and press a plate or gauze against the wound for therapeutic purposes.

IX. This unit may also be combined and used with any other methods or means of generating pressure and force that can be possibly used by this system in order to provide the needed force and pressure on the wound site.

Pressure measuring devices.

Any proper pressure measuring devices may be used with these systems; they can be mechanical, electrical or electronical.

The inflation system of these units.

The inflation of the balloons may be done by:

1. A commonly used inflation bulb.

II. By the connection of the balloons to a pressurized air or a gas tank of different sizes, having enough safety means and controls.

II. Syringes or pumps may be utilized as well to inflate the balloons or inject the liquids. Special syringes may be made to function like a hand-held pump to both inflate the balloon easily and to suction the air quickly out as well.

IV. A foot pump connected to a regular bulb may be used as mentioned in the inventor's application of "dual powered pressure inflation unit and the method."

VI. An electrical pump may also be used to fill the balloon as well. These will be designed to conveniently fill the balloon and have safety measures to prevent overinflation and gauges to allow proper observation of the pressure. These units may be connected and used with the use of a computer in order to allow the level of air and its adjustments and alarm set up all to be done by an advanced program.

An alarm means may also be incorporated in the system to inform of unwanted pressure changes in the system or the balloons. Safety valves may be used as well. A control system will also be used with the pressurized tanks to prevent pressure from exceeding a certain pre-determined ceiling. Automatic shut-offs may be incorporated into these control means when needed.

V. A programmable, computerized unit with electronic or other sensors means may be used to sense the pressure and allow an automatic and programmable unit to be utilized. This unit will have a signal or alarming system to allow the changes in the pressure to be noticed. This unit will be programed to automatically change the pressure of the balloon according to a program which was formerly given. The computer technology will also allow many predetermined programs to be used for a desirably individualized plan.

This computer will consist of at least the following elements:

a. An electric pump to make pressurized air.

b. A series of safety valve means to prevent the pressure of the system from exceeding a preset level.

c. A series of sensor means to allow the pressure of the system to be sensed. This will be connected to a computer program both for setting a limit and to reacting to the pressure as well.

d. An alarm or a signal means to notify the staff from certain events.

e. A mini computer that will allow programming to be done.

f. A series of valves means to allow the movement of the air to be directed in the desired direction and controlled.

Importantly, such a computer will allow the initial high pressure to be applied for a period of time and then to decrease pressure to a lower level and maintain it for as long as it is desired. The computer will allow the staff to know if there is an unscheduled drop in the pressure of the balloon and it may be scheduled to inflate the system if bleeding occurs. Therefore, such a unit will decrease the dependency for the medical staff which is very costly.

Other uses of such a support and compression system.

Importantly, this system may be used to compress a special dressing or medication against the skin or the wound of a patient in order to allow it to be absorbed more quickly or abundantly. This applicant has suggested this idea in his previous applications. What he suggest is to use the following methods:

A. First, a film or layer of the medication is to be applied to the wound area or the skin.

B. The medication film will be covered by a thin layer of non-irritant protection layer such as gauze pad, vinyl or paper.

C. Then, a properly sized and shaped support and balloon unit will be used in order to allow the pressure to be applied on the medicated area.

D. The magnitude of the pressure will be properly decided in order to prevent compromising the circulation of the area.

Such a therapy will be useful in providing medications such as nitroglycerine ointments to the body or certain other medications in skin disorders such as ulceration, chronic diseases such as psoriasis, etc.

The units for detection of the bleeding.

The idea of detecting bleeding in the wound by use of electrical methods was first introduced by this applicant in his application for D. Device 3. Another model of that idea was also introduced in the application of D. Device 8. In this application this idea is explained as well and the model which is shown allows the use of a gauze pad with the capacity to detect the bleeding alone or in combination with the compression unit. A model of a gauze pad that can detect bleeding is schematically shown in FIG. 6. This Figure shows the cross-cut view of a gauze pad 37 that has the sensor leads M and N inside connected to an electrical system and the presence of blood between these leads will cause an electrical circuit to be activated and signal means to announce it. In this unit the presence of the blood between these electrodes due to its physical or chemical nature will cause the electricity to pass through the space between the electrodes M and N to make the electrical circuit complete and give the signal. This signal can be an alarm or any other pre-designed signal means. This gauze pad is covered by a clear impermeable layer 32 that has a rim or border 33 and 34 which goes all around the gauze pad. The surface of this band toward the skin is covered by a film of adhesive shown at 35 and 36. This band of adhesive will allow this unit to be adhered to the skin around the wound in order to seal the area. In some models the surface of the gauze pad may also have a film of adhesive film on it such as one marked at 38 so that it will allow the gauze pad to adhere to the skin and stand in the area more securely, and in order to keep the skin tight. Thus, this action will also participate in preventing from bleeding in the wound site. The adhesive film may be made in the shape of a screen or it may have openings or mini holes in it in order to allow the blood to trans-pass and reach the sensor leads. The electrical signals may be used alone or it may be altered or amplified by computers and different units to cause different functions to occur. The computer will allow many actions to be taken such as informing the medical staff from the event of pumping a compression unit to function, etc. The compression unit may use an air pump and a series of pressure sensors and controls to pump the air into a balloon-operated compression unit. This will inflate the balloon automatically if the bleeding is detected. Importantly, this gauze pad unit may have more than one electrode in it in order to allow signals from different areas to be detected and differentiated properly. Also, different electrodes may allow for detection of different signals as well. A multiple electrode system may be used to allow for occurrences such as the expansion of the bleeding. Also, importantly these units may have different layers of gauze pads to allow some degree of absorption of the sweat or wound secretions before they reach the sensor area, so that this mechanism will prevent the alarm from sounding due to sweat or other minor secretions. Importantly, these gauze pads or parts of the gauze pads may be impregnated with different chemicals or can have other physical materials or other means in order to allow differentiation between different materials and secretions from the wound site to occur. Importantly, these gauze pads may also have a piece of rigid, transparent wound piece in their body in order to allow for compression of the wound area. The wound piece may have any proper shape and size and can be placed in any proper part of these pads. FIG. 7 schematically shows how a bleeding detection system will function. In this Figure, the upper electrode M is shown and is a larger piece that goes over the lower electrode N shown with a dashed line. The center of the unit shown at area 32 may have an opening to allow the color of the gauze pad to be seen as well. If bleeding occurs, the blood will be absorbed by the gauze pad and will enter the space between the electrodes M & N. These electrodes are connected by an electrical connection means to a mini-computer symbolically shown at 39 which will analyze the signals and may amplify or modify it and initiate a series of pre-designed actions such as: causing an alarm to sound, the patient to be informed, the patient to receive directions to follow, an electrical pump to inflate the compression balloon, etc. In this Figure, the electrodes M and N are shown, the mini-computer is marked at 39, the alarm inside the computer is marked at 40 and the battery at 41. This system may also use a control mean such as a button at the bedside to allow an alert patient to inflate the compression balloon to apply pressure in the wound. The patient may also use the control unit as part of relaying the information to the medical staff via a proper network.

Importantly, the gauze pad between the electrodes may be treated with certain chemicals or materials in order to influence, exaggerate or modify the effect of the blood in the area for a better chemical, electrical, physical detection or any other kind for that matter.

Also, in different models these chemicals may be changed to allow different secretions to be identified such as secretions from wounds, amniotic fluids, etc. The sensor method may also differ in different models; it may use any sensors (physical, chemical, optical, etc.), in order to identify or modify the signals.

Importantly, some models of these units may be made to use the physical presence of the blood in the area for the signal production; this will be done with respect to the following issues:

a. The presence of blood will increase the pressure in the area so that this effect will be used to produce the signal by the use of pressure sensors in the area or inside the gauze pad. This change in the area's pressure will be detected and relayed to a signal alteration unit such as a computer.

b. The absorption of the blood by a dry gauze will make hydrophylic fabrics such as cotton to swell. This will increase the volume of that piece and the expansion will also increase the pressure of the swollen part in the area. These two effects will be used to produce the signal by the use of sensors that will detect the increase in volume (multiple versions of such units may be made; for example, the increase in volume may separate two electrodes or by the use of a lever system may make electrodes touch each other in order to initiate or alter an electrical signal) and/or increase in the pressure in the area so that the change in the volume or pressure of the area will be detected and relayed to a proper signal alteration unit such as a computer.

c. The presence of blood will change the color of the area and this will produce different wave lengths of light that may be detected by the use of proper sensors in order to allow them to be known and to affect a proper signal alteration unit such as a computer.

These gauze pads may be used in different stages of wound care. These units may have connection means between the compression unit and the sensory pieces, so that after the compression unit is used in the early stage of control of the bleeding, the gauze pads will be used to continue a safe therapy.

Importantly, the size, width, thickness, coloring, relative thickness of the particular areas, and the walls, hardness, shape, materials and every other important characteristics of these units may vary in different models in order to make different units available for use in different patients and conditions.

I claim:

1. A device for protecting a wound site on the exterior of a body comprising:

a) a non-stretchable cover adapted to cover an underlying wound site on the exterior of a body;

b) a support system for supporting said cover so that said cover is held against the exterior of a body in covering relation to an underlying wound site;

c) said support system comprising a first strap means and a second strap means both of which strap said cover to the exterior of a body;

d) wherein said first strap means and said cover together form a girdling portion that girdles a portion of a body to exert a girdling force holding said cover against the exterior of a body in covering relation to an underlying wound site;

e) wherein said second strap means forms a non-girdling portion that does not girdle a portion of a body and that acts on said girdling portion in a direction that is transverse to said girdling portion; and f) wherein said girdling portion comprises means for setting a desired effective length of said first strap means and includes means for allowing said girdling portion to be wrapped around and unwrapped from a portion of a body.

2. A device as set forth in claim 1 wherein "a separable attachment means" is embodied in said means for setting a desired effective length of said first strap means.

3. A device as set forth in claim 2 wherein an attachment piece on said first strap means and a complementary attachment piece on said cover provide the embodiment of "said separable attachment means" in said means for setting a desired effective length of said first strap means.

4. A device as set forth in claim 3 wherein said cover comprises a tab projecting outwardly from a central portion thereof and said complementary attachment piece on said cover is disposed on said tab.

5. A device as set forth in claim 1 wherein said cover comprises a plurality of tabs projecting outwardly from a central portion thereof, a respective attachment portion is disposed on each of said plurality of tabs, said first strap means comprises a complementary attachment portion for attaching to the attachment portion on one of said tabs, and said second strap means comprises a complementary attachment portion for attaching to the attachment portion on another of said tabs.

6. A device as set forth in claim 1 wherein said cover comprises two points of separable attachment of said first strap means thereto, and a third point of separable attachment of said second strap means thereto.

7. A device as set forth in claim 6 wherein said two points of separable attachment of said first strap means to said cover are directly opposite each other, and said third point of separable attachment of said second strap means to said cover is intermediate said two points of separable attachment of said first strap means.

8. A device as set forth in claim 1 wherein said cover comprises a perimeter that comprises means providing a number of attachment points for the selective attachment of said first strap means and said second strap means to particular ones of said attachment points.

9. A device as set forth in claim 8 wherein said means providing a number of attachment points for the selective attachment of said first strap means and said second strap means to particular ones of said attachment points comprises a band extending continuously around said perimeter.

10. A device as set forth in claim 1 wherein said cover comprises a dome shape for fitting to a dome-shaped portion of a body.

11. A device as set forth in claim 1 wherein said cover comprises a formable material that can be shaped at the time of application of the device to a body for fitting to the shape of the portion of a body to be covered.

12. A device as set forth in claim 1 wherein said cover comprises a rigid, pre-formed shape for fitting to a body.

13. A device as set forth in claim 1 wherein said cover comprises a frame having an opening, and a closure for opening and closing said opening.

14. A device as set forth in claim 13 wherein said closure comprises a door having its own frame for fitting in overlapping relation to the frame of said cover.

15. A device as set forth in claim 13 further including a balloon means disposed beneath said cover.

16. A device as set forth in claim 1 wherein said cover comprises a transparent portion allowing viewing through said cover.

17. A device as set forth in claim 16 further including a transparent balloon means disposed beneath said transparent portion of the cover, and a wound piece disposed beneath said balloon means.

18. A device as set forth in claim 1 including an absorbent pad beneath said cover, and said absorbent pad being at least partially enclosed in a non-permeable polymer which has a surrounding trough for collecting secretions from the wound.

19. A device as set forth in claim 1 including a pocket on the outside of said cover for holding and locating wound treatment accessories inside.

20. A device for protecting a wound site on the exterior of a body comprising:
  a) a cover for covering a wound site on the exterior of a body;
  b) a support system for supporting said cover so that said cover is held against the exterior of a body in covering relation to an underlying wound site;
  c) said support system comprising a first strap means and a second strap means both of which strap said cover to the exterior of a body;
  d) wherein said first strap means and said cover together form a girdling portion that girdles a portion of a body to exert a girdling force holding said cover against the exterior of a body in covering relation to an underlying wound site;
  e) wherein said second strap means forms a non-girdling portion that does not girdle a portion of a body and that acts on said girdling portion in a direction that is transverse to said girdling portion;
  f) wherein said girdling portion comprises means for setting a desired effective length of said first strap means and includes means for allowing said girdling portion to be wrapped around and unwrapped from a portion of a body; and
  g) a number of finger-grippable tabs distributed over the outside of said cover that can be gripped to facilitate placement of said cover.

21. A device for protecting a wound site on the exterior of a body comprising:
  a) a non-stretchable cover for covering a wound site on the exterior of a body;
  b) a support system, comprising a first strap means and a second strap means, for supporting said cover so that said cover is held against the exterior of a body in covering relation to an underlying wound site;
  c) said first strap means having opposite ends attached to said cover for girdling a portion of a living body, at least one of which ends comprises fastening means providing for its separable adjustable fastening to said cover to adjust the effective length of said first strap means;
  d) said second strap means having opposite ends, at least one of which ends comprises fastening means providing for its separable adjustable fastening to said cover; and
  e) wherein complementary fastening means are affixed to the cover to provide for the separable adjustable fastening of said at least one end of each of said first and second strap means.

22. A device as set forth in claim 21 wherein said fastening means on said strap means and said complementary fastening means on said cover are complementary Velcro (tm) fastener strips respectively.

23. A device as set forth in claim 22 wherein the fastening means on the cover are disposed as tabs projecting from the perimeter of the cover.

* * * * *